(12) United States Patent
Popov et al.

(10) Patent No.: US 7,422,572 B2
(45) Date of Patent: Sep. 9, 2008

(54) COMPACT CATHETER INSERTION APPARATUS

(75) Inventors: Sergey Popov, Beer-Sheva (IL); Leonid Lukov, Beer-Sheva (IL)

(73) Assignee: Serpomed Ltd., Beer-Sheva (IL)

( * ) Notice: Subject to any disclaimer, the term of this patent is extended or adjusted under 35 U.S.C. 154(b) by 201 days.

(21) Appl. No.: 10/468,545

(22) PCT Filed: Feb. 17, 2002

(86) PCT No.: PCT/IL02/00119

§ 371 (c)(1),
(2), (4) Date: Aug. 20, 2003

(87) PCT Pub. No.: WO02/066093

PCT Pub. Date: Aug. 29, 2002

(65) Prior Publication Data

US 2004/0116855 A1     Jun. 17, 2004

(30) Foreign Application Priority Data

Feb. 21, 2001     (IL) .................................... 141574

(51) Int. Cl.
*A61M 5/32* (2006.01)
(52) U.S. Cl. .................................... 604/198
(58) Field of Classification Search .................. 604/35, 604/272, 161, 162, 164.01, 164.02, 164.05, 604/164.06, 164.07, 164.08, 168.01, 192–198, 604/257, 263, 409, 900, 65–67; 128/DIG. 12, 128/DIG. 13; 600/384, 386, 393, 491, 499, 600/546, 547, 591, 554
See application file for complete search history.

(56) References Cited

U.S. PATENT DOCUMENTS 2,876,770 A    3/1959    White (Continued)

FOREIGN PATENT DOCUMENTS

EP    0 494 779    7/1992

(Continued)

OTHER PUBLICATIONS

International Search Report and Written Opinion for International Application No. PCT/US2005/014217 mailed Aug. 11, 2005.

(Continued)

*Primary Examiner*—Manuel Mendez
(74) *Attorney, Agent, or Firm*—Renner, Otto, Boiselle & Sklar, LLP

(57) ABSTRACT

Invention relates to catheter placement devices for peripheral blood vessel catheterization with protected needle tip and shortened length in a transport position (see FIG. 31). In the transport position (FIG. 9), the needle and catheter units (1 and 5) are held inside the handle (8). User transposes the needle and catheter units into a duty ready position (FIG. 6), wherein the needle unit is engaged with the handle distal end and a catheter hub (7) protrudes distally out of the handle. After catheter insertion into patient vein, user disconnects the needle unit and handle allowing the needle unit retraction by a resilient member (11) into the protection position. The trigger and transposing means (22) location enables the apparatus single handed control. The fixation means (31) in the protection position eliminates repeated needle unit advance. It can be used rubber or spiral spring resilient members and the catheter hubs with foldable side wings and side port.

31 Claims, 14 Drawing Sheets

U.S. PATENT DOCUMENTS

| | | |
|---|---|---|
| 3,046,985 A | 7/1962 | Saenz |
| 3,314,428 A | 4/1967 | Johnson et al. |
| 3,890,971 A | 6/1975 | Leeson et al. |
| 4,542,749 A | 9/1985 | Caselgrandi et al. |
| 4,654,031 A | 3/1987 | Lentz |
| 4,747,831 A | 5/1988 | Kulli |
| 4,988,339 A | 1/1991 | Vadher |
| 5,259,590 A | 11/1993 | Chambers |
| 5,279,590 A | 1/1994 | Sinko et al. |
| 5,480,385 A | 1/1996 | Thorne et al. |
| 5,695,476 A | 12/1997 | Harris |
| 5,807,309 A | 9/1998 | Lundquist et al. |
| 5,902,280 A | 5/1999 | Powles et al. |
| 6,086,563 A | 7/2000 | Moulton et al. |
| 6,224,576 B1 | 5/2001 | Thorne et al. |
| 6,436,070 B1 | 8/2002 | Botich et al. |
| 6,461,362 B1 * | 10/2002 | Halseth et al. ............... 606/108 |
| 6,582,402 B1 | 6/2003 | Erskine |
| 2002/0151847 A1 | 10/2002 | Takagi et al. |

FOREIGN PATENT DOCUMENTS

| | | |
|---|---|---|
| EP | 0 494 779 A1 | 7/1992 |
| EP | 0 545 671 | 6/1993 |
| EP | 0 545 671 A1 | 6/1993 |
| EP | 0 931 561 | 7/1999 |
| EP | 0 931 561 A2 | 7/1999 |
| EP | 1 075 850 A2 | 2/2001 |
| FR | 2 846 244 | 4/2004 |
| WO | 99/16488 | 4/1999 |
| WO | 02/066093 A2 | 8/2002 |

OTHER PUBLICATIONS

Supplementary European Search Report for European Application No. 02 71 2221 dated Nov. 24, 2006.

Supplementary European Search Report for European Application No. 02 71 2221 dated Nov. 24, 2006.

European search report for Application No. 02 712 221.7 dated Jun. 11, 2007.

European search report for Application No. 02 712 221.7-2310 dated Jun. 11, 2007.

* cited by examiner

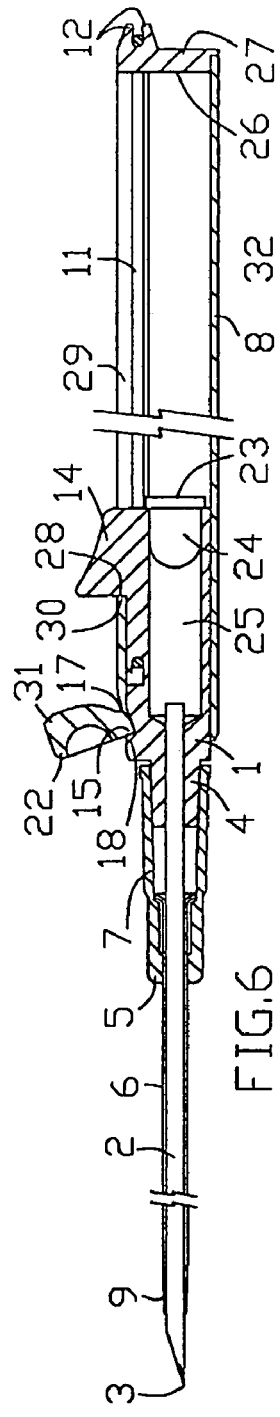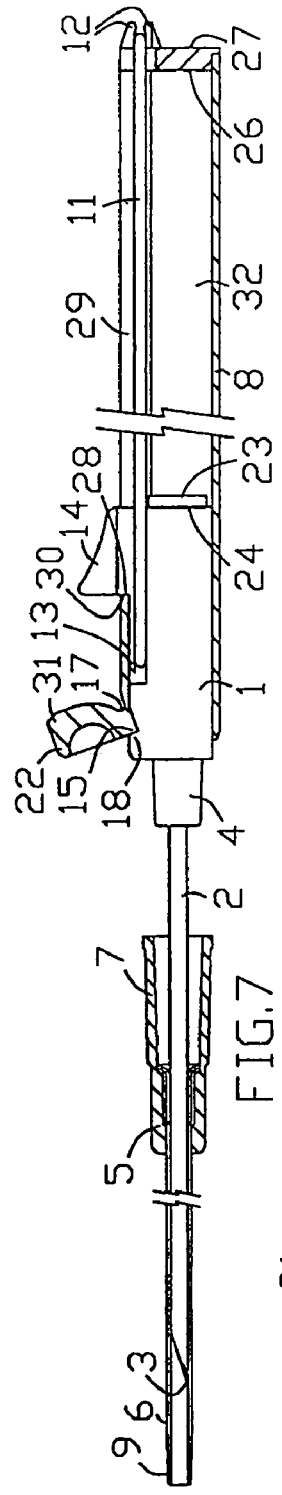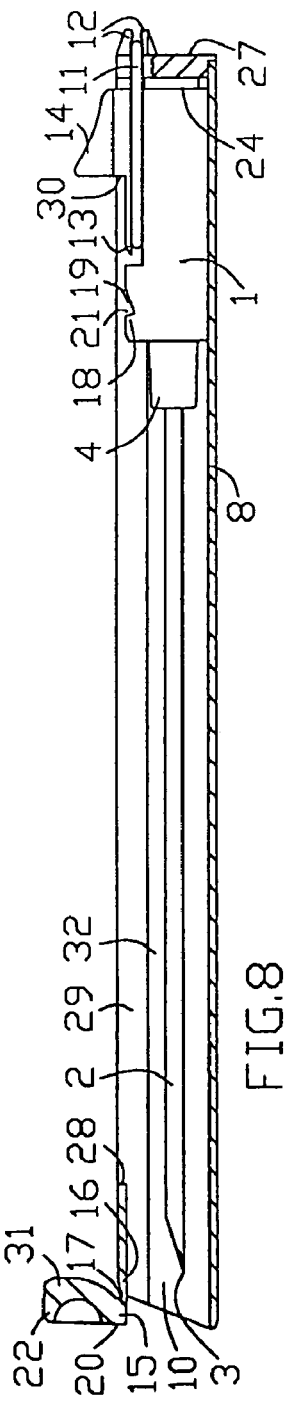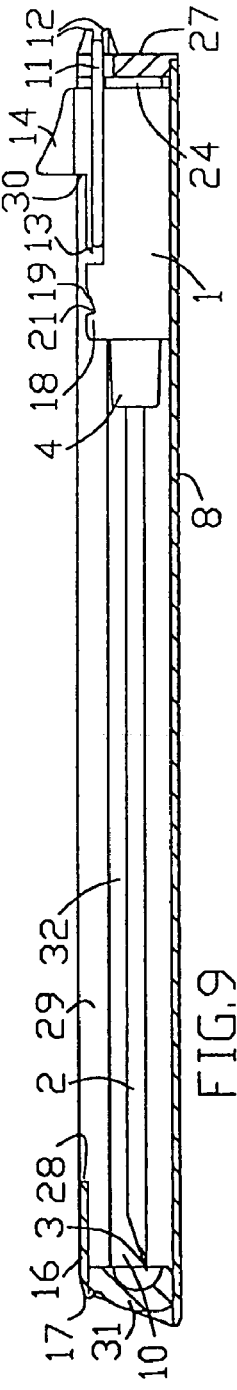

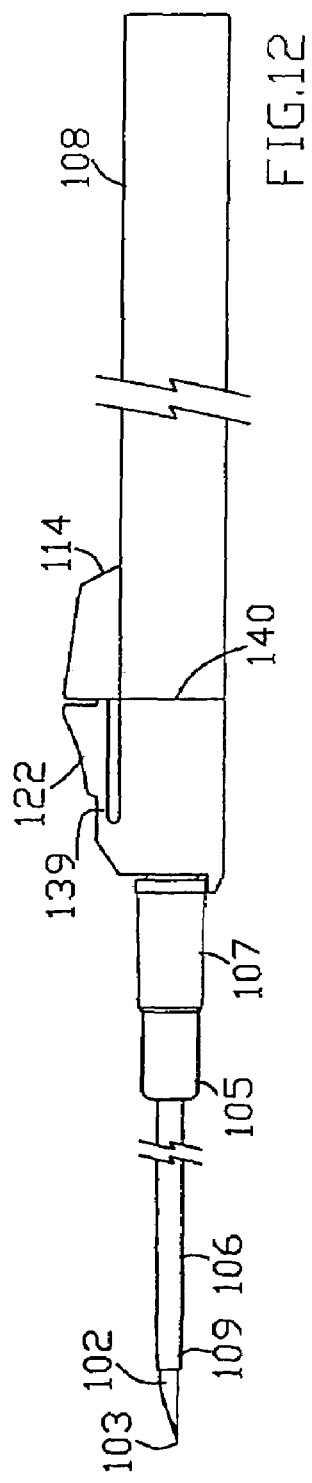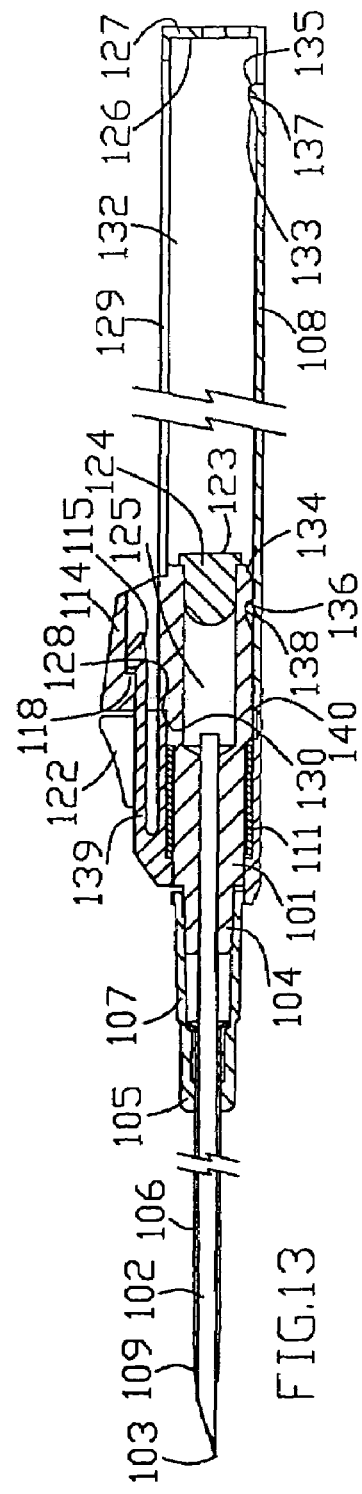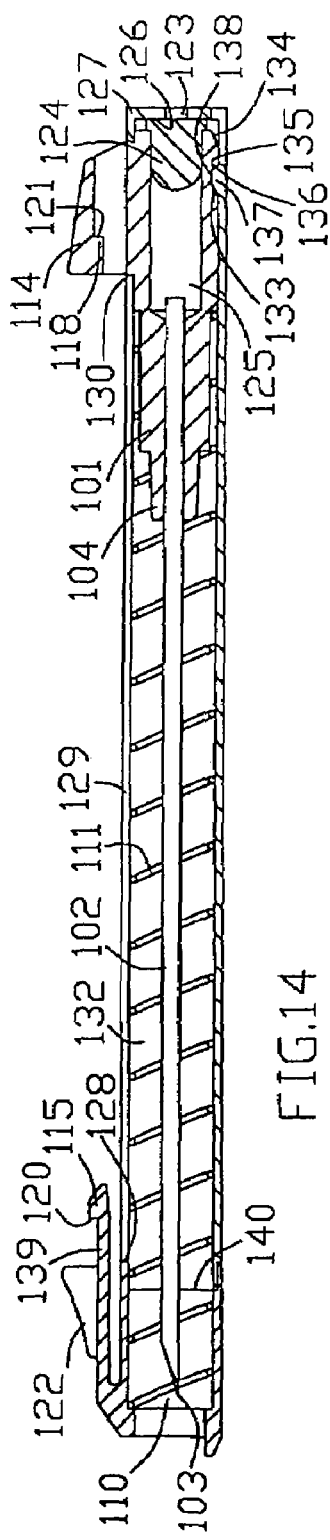

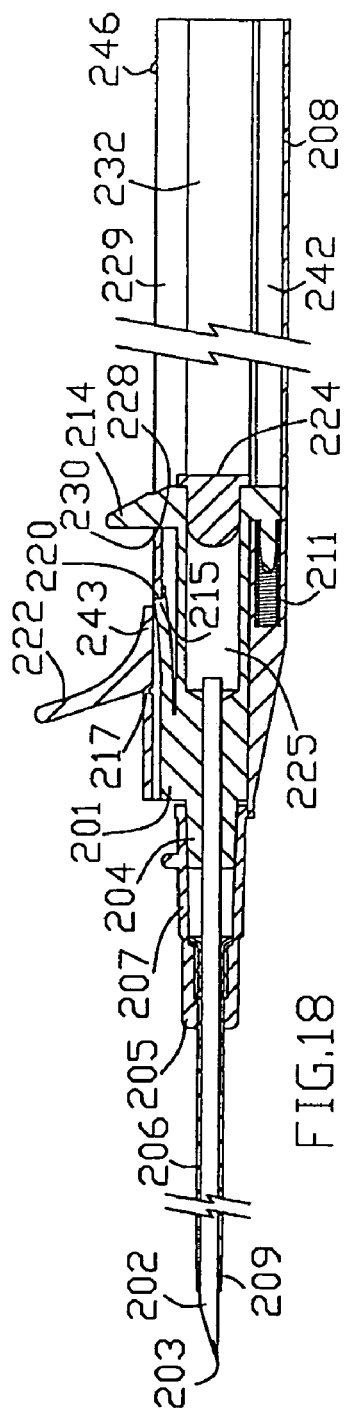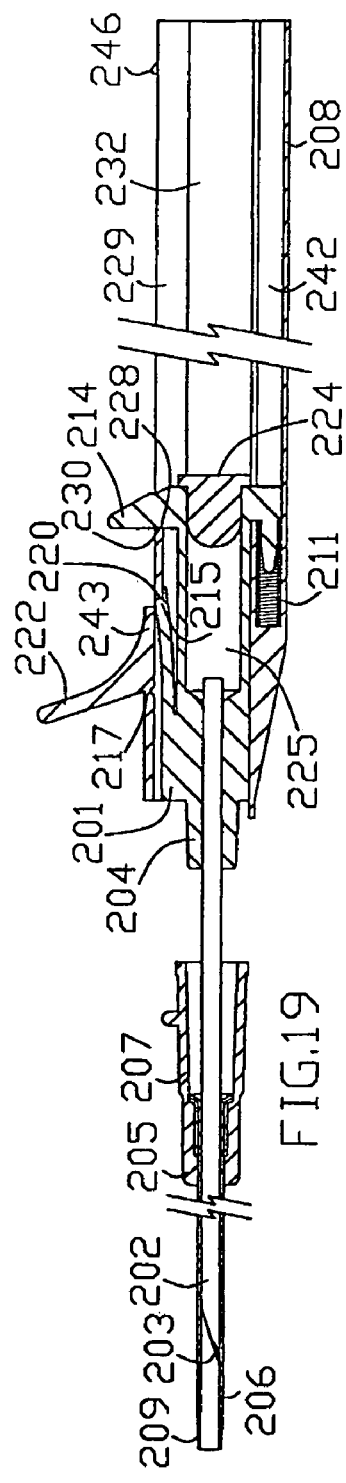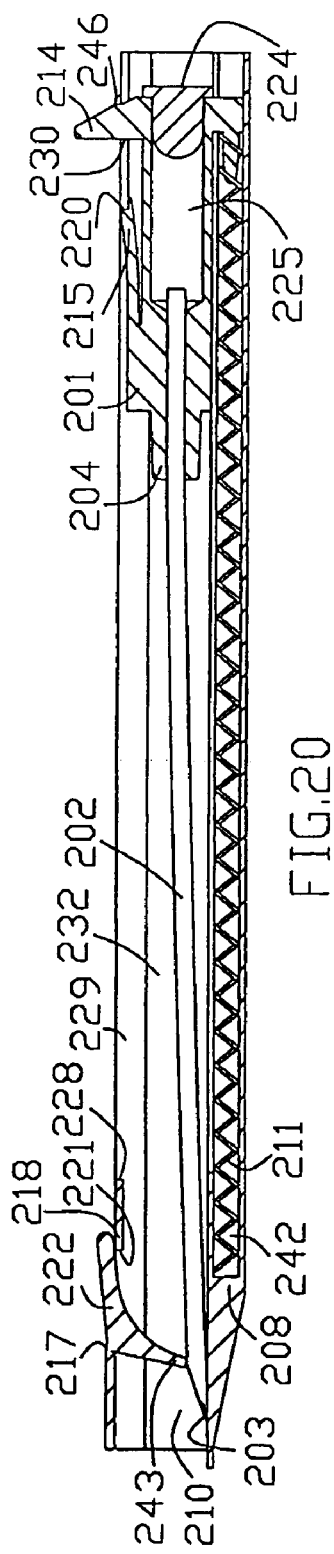

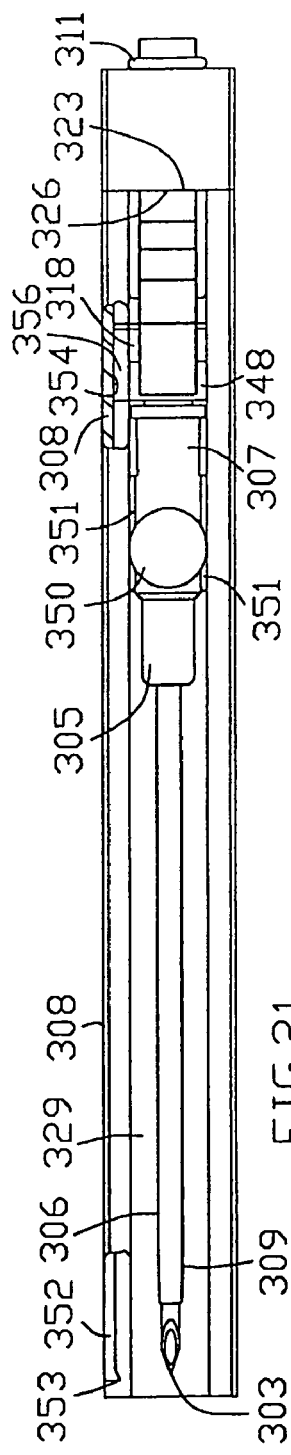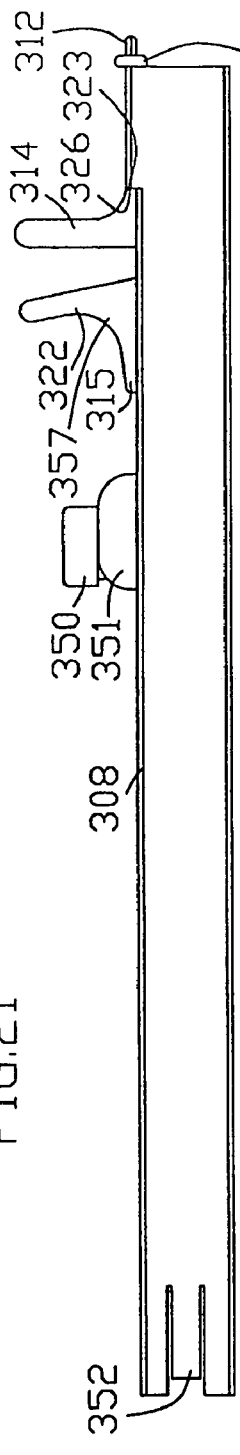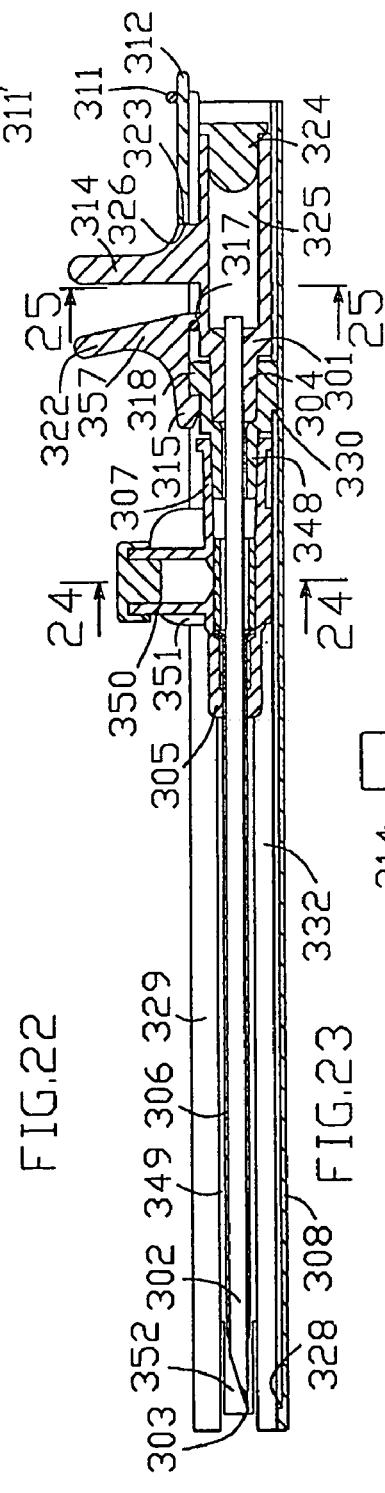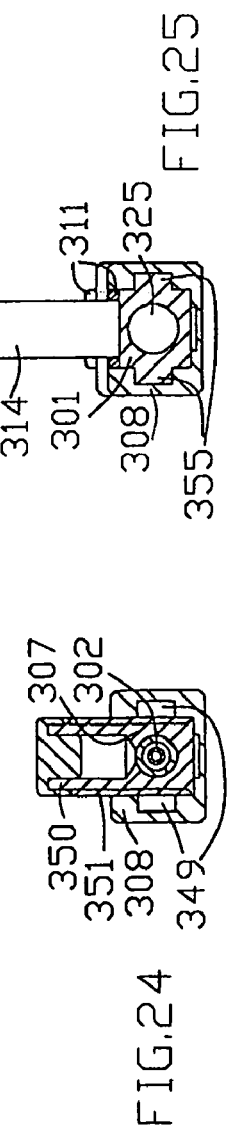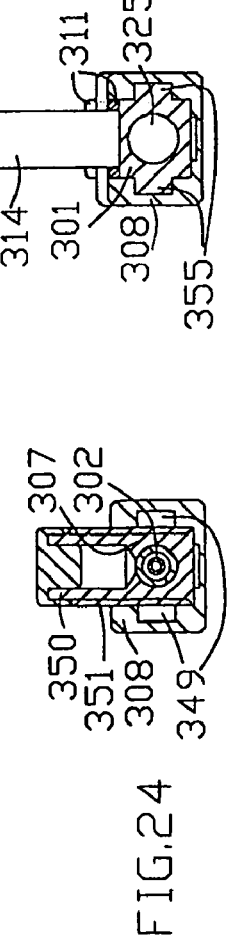

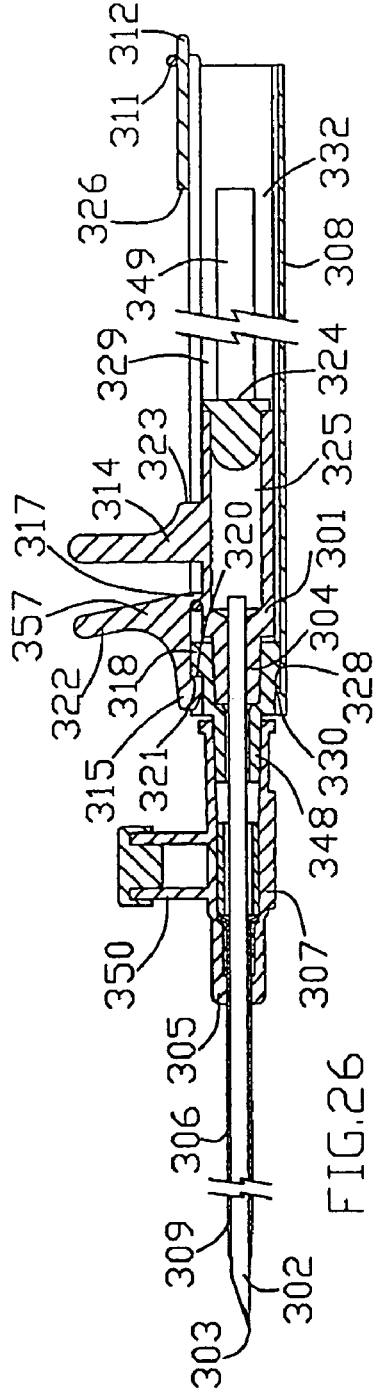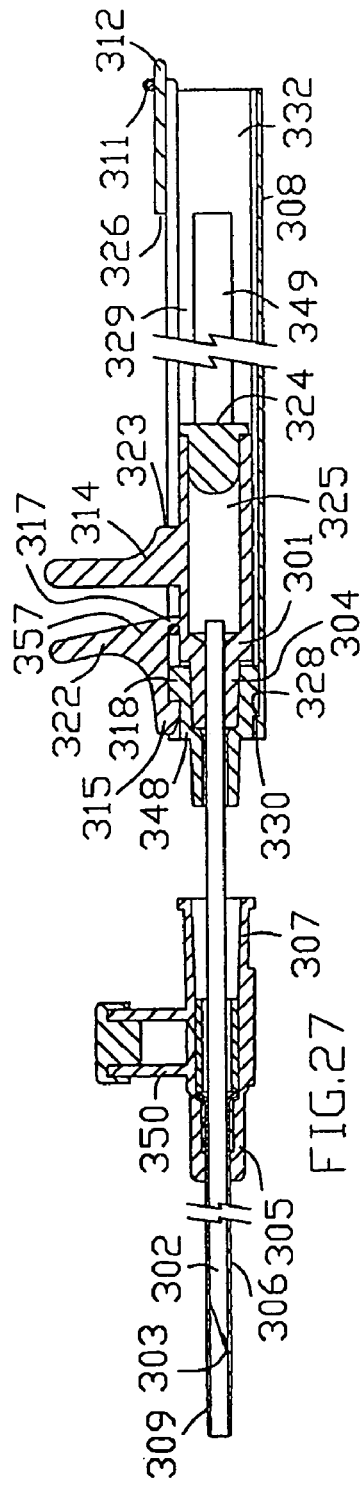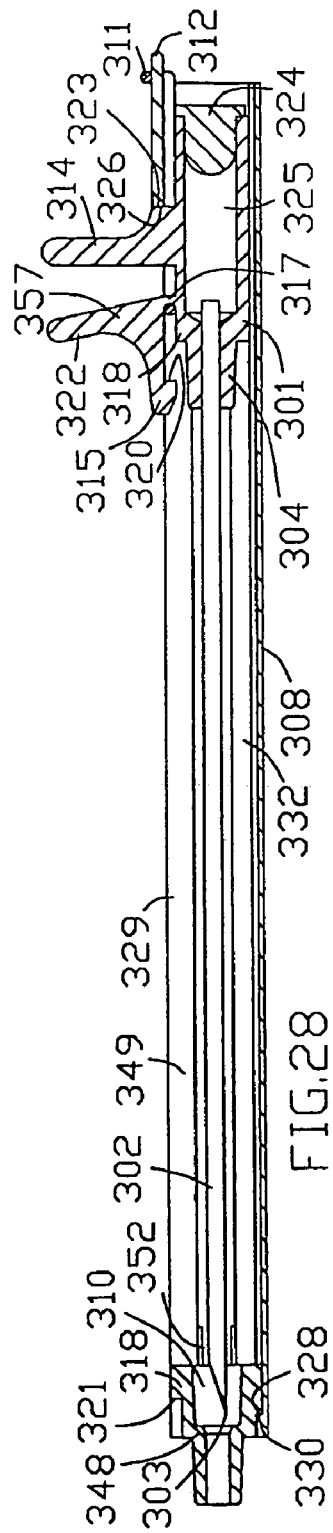

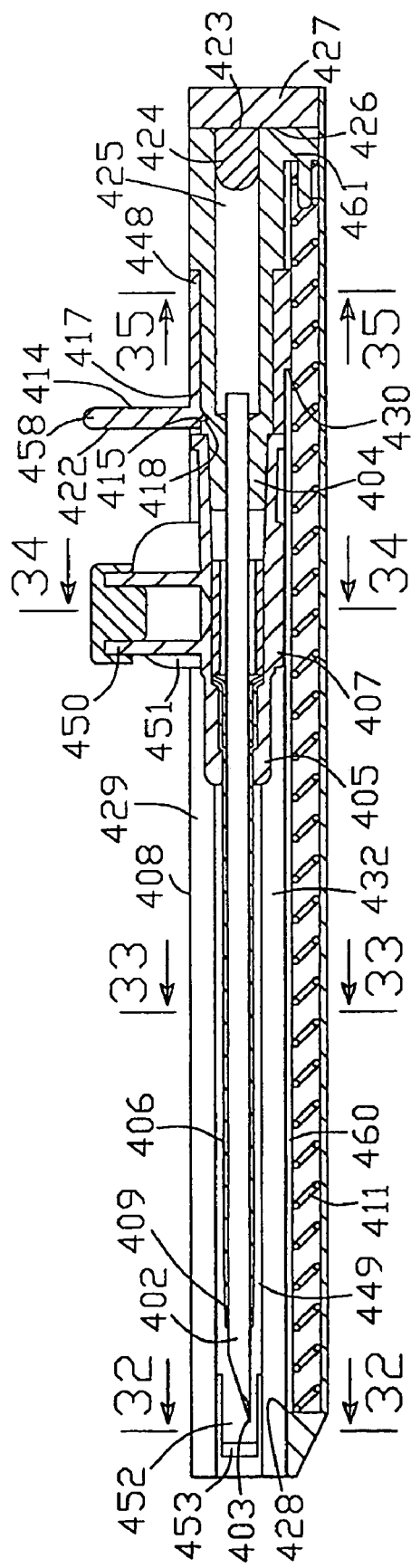
FIG.31
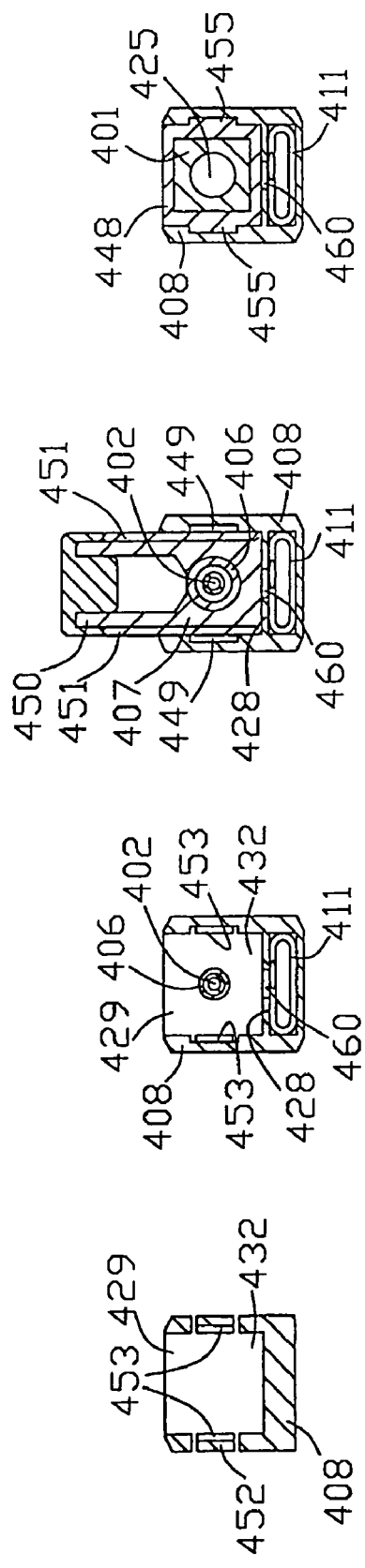
FIG.33
FIG.34
FIG.35
FIG.32

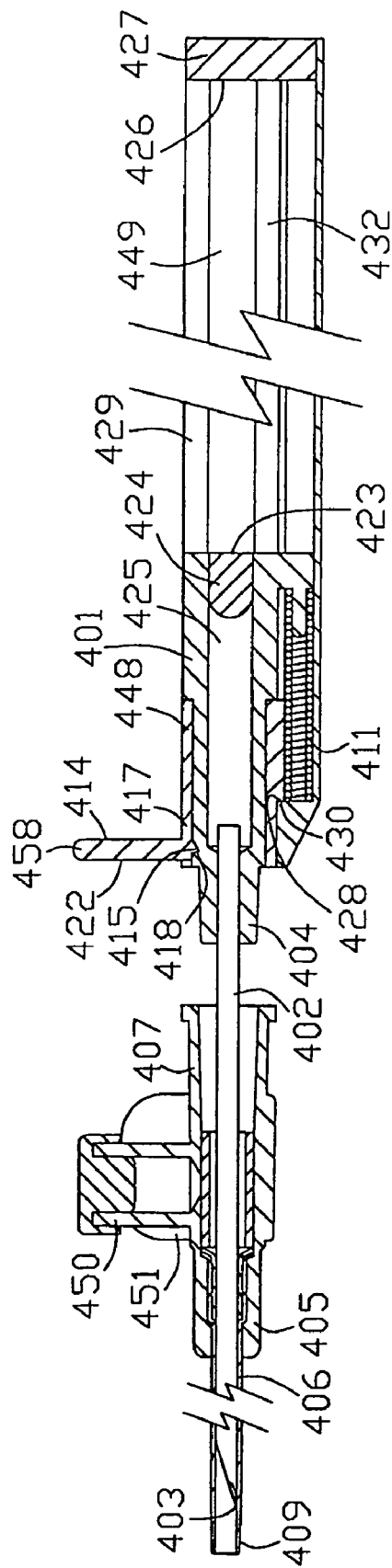
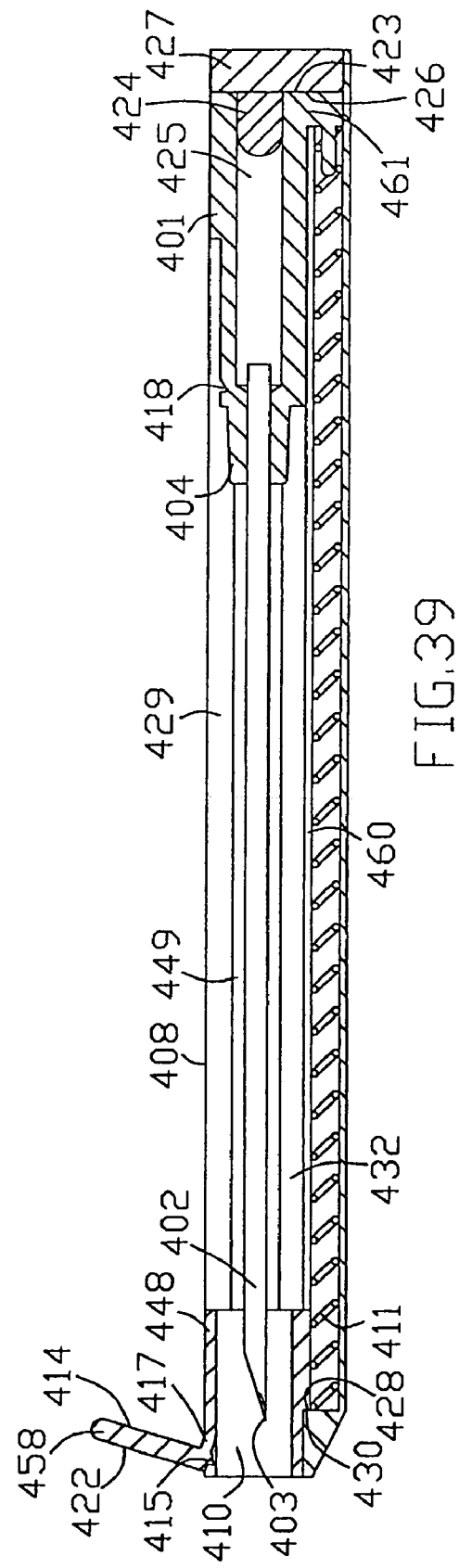
FIG.38
FIG.39

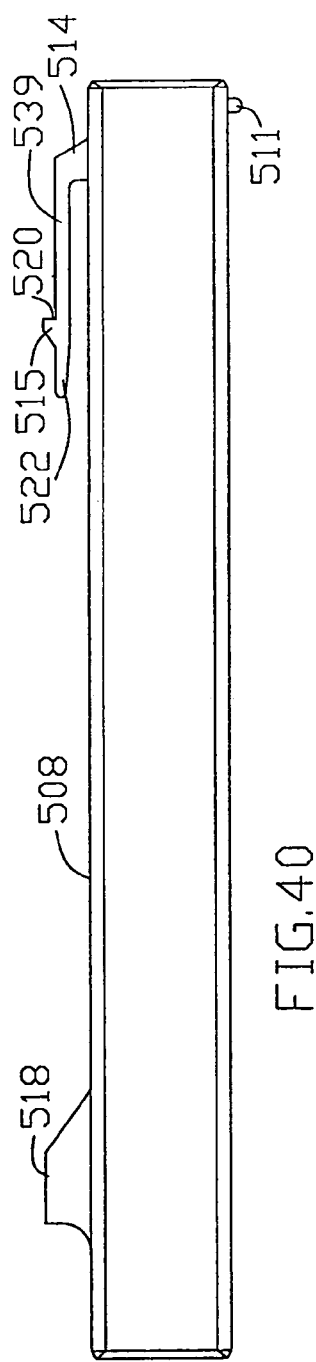
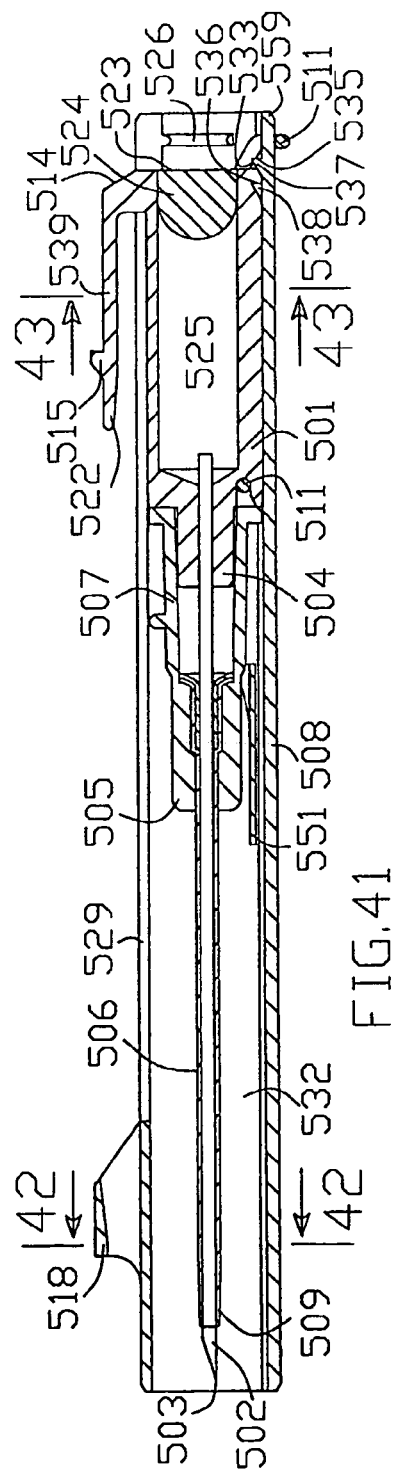
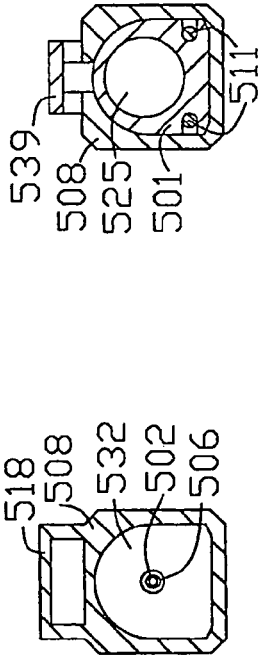
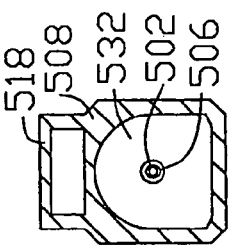
FIG.40
FIG.41
FIG.42
FIG.43

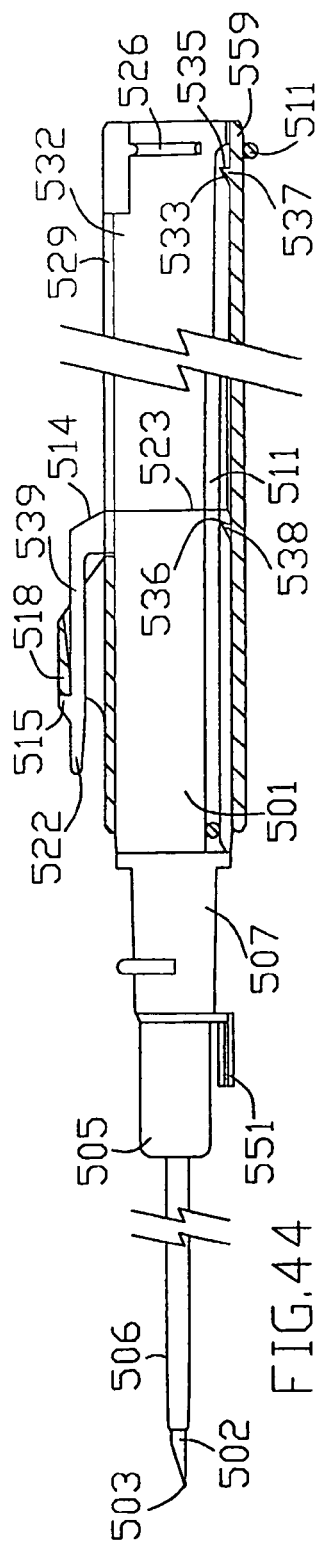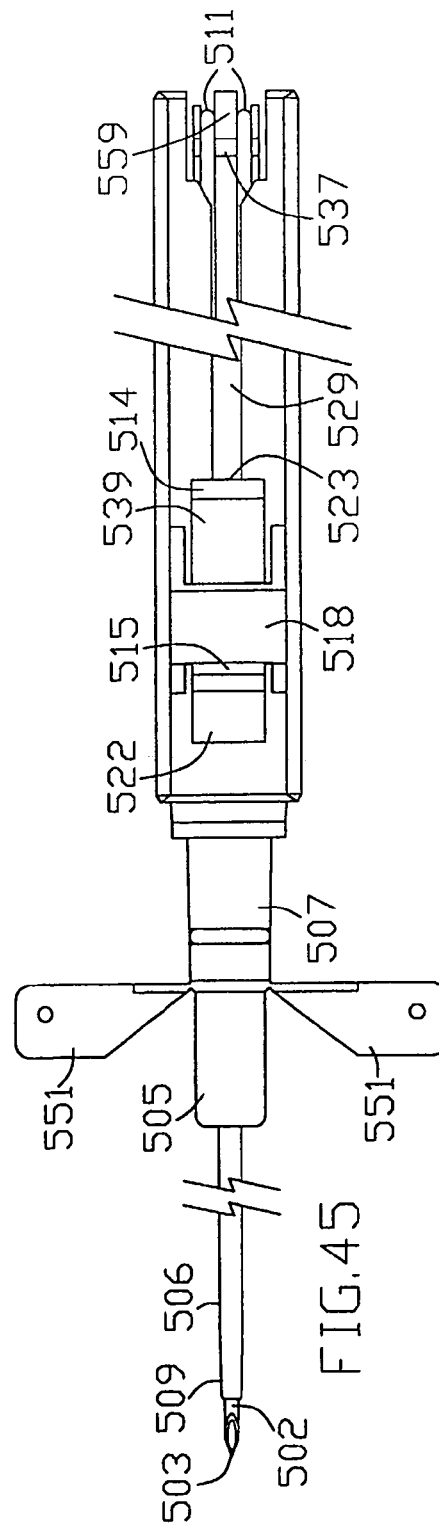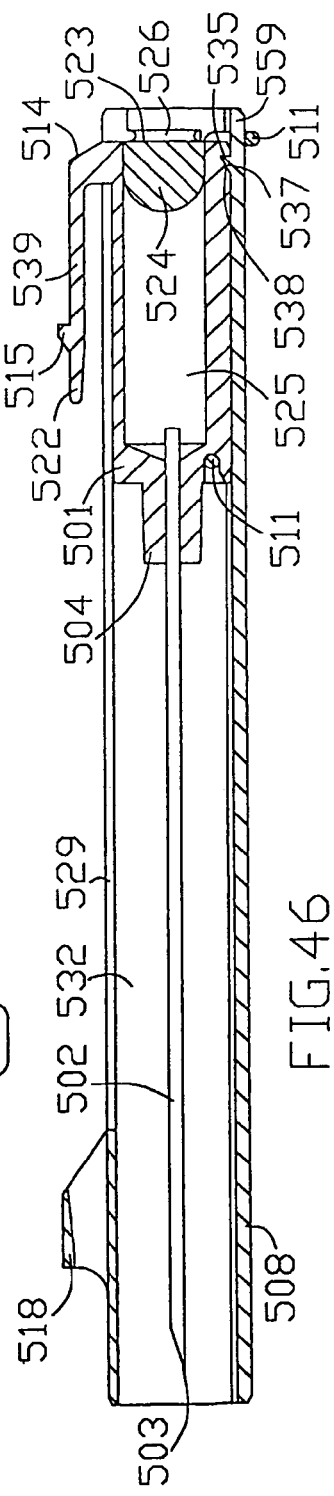

COMPACT CATHETER INSERTION APPARATUS

This application is a national phase of International Application No. PCT/IL02/00119 filed Feb. 17, 2002 and published in the English language. Priority of Israel patent application No. 141574 filed Feb. 21, 2001 also is claimed via the aforesaid International Application.

FIELD OF INVENTION

This invention generally relates to the catheter placement devices for intravascular catheterization and more particularly to the catheter insertion apparatus for peripheral blood vessel catheterization with a needle tip protective system and shortened length in the transport position.

BACKGROUND

The catheter insertion apparatus for intravascular catheterization includes, as a rule, a catheter unit with a catheter tube and a catheter hub, a needle unit with a tubular needle and a needle hub as well as a hollow handle. Prior to use in the duty ready position, they are assembled so that the sharp distal point of the needle extends beyond the distal end of the catheter tube and the catheter tube extends beyond the distal end of the hollow handle. The user advances the catheter into the blood vessel and withdraws the needle unit leaving the catheter in the blood vessel. To prevent the user from being pricked, the withdrawn needle is transposed into the protection position avoiding the transmission of the infection by the blood contaminated needle. In this position, the needle unit is disposed inside the hollow handle and the needle sharp distal point is disposed in a security zone ruling out contact by the user with said sharp distal point. Thus, prior to use, the device has a relatively long length, which approximately is equal to the sum of the hollow handle length and the catheter unit length. In the protection position, the apparatus is substantially shorter because the needle unit is housed inside the hollow handle. In the development of modern catheter placement devices, there has been a tendency to reduce the device length in the transport and storage positions as well. This provides definite advantages such as the lower packaging and transportation cost. In said transport position, the device is compact because the catheter unit and the needle unit are positioned inside the hollow handle. Immediately before use, the apparatus is converted into the above duty ready position. Mentioned compact catheter insertion apparatus has to meet the following requirements:

- Minimal length at the transportation and storage stages;
- Easy conversion into the duty ready position;
- Convenience of catheter placement;
- Minimal number of unusual, non-customary manipulations;
- Possibility of one handed trigger activation allowing for apparatus retraction into the protection position using the same hand which holds the apparatus;
- Reliability of triggering off the means retracting the needle unit into the protection position;
- Low manufacturing cost due to the easy of details fabrication and their assembly and also the decrease of the details number and material consumption.

There are many catheterization devices having mentioned transport, duty ready, and protection positions.

U.S. Pat. No. 4,988,339 discloses Retractable needle/syringe devices for blood collection, catheterization and medicinal injection procedures. The devices are comprised the needle unit in the form of a syringe and the catheter unit received in an oblong hollow handle with a retracting spring disposed in the hollow handle distal portion around the needle coaxially to it and the pusher of the needle unit, disposed axially at proximal handle face. The pusher is designed for manual transposition of the needle unit from the transport position into the duty ready position. The hollow handle is provided with slots for the transposition inside them a manual controlled drive of syringe piston and trigger member. The latter is designed for the control of needle unit retraction into the duty ready position. The disadvantage of this device is its great length caused by the needle unit pusher, which, in the transport position, protrudes in proximal direction and thereby increases the device length. Moreover, the necessity to provide the definite stroke of the syringe piston drive adds to the devices length and leads to the growth of material consumption. Another disadvantage is the absence of direct access to the catheter hub in the duty ready position (see FIG. 5 of U.S. Pat. No. 4,988,339). This impedes the control of the catheter by the user during catheter insertion into the patient's vein. Another disadvantage is the mutual disposition of the handle, the trigger member, and the pusher ruling out the possibility of the device control by the same hand, which holds the device. The device consists of many details including the proximal lid of the handle and the pin of the syringe piston drive, demanding separate fabrication and assembly. Other part of the details, such as the handle, syringe barrel, and piston, include many slots and notches, which significantly complicate their fabrication. As a result, the manufacturing cost of the device grows substantially. Another disadvantage is the possibility of the needle unit exit from the protection position as a result of the action onto accessible pusher and fixation means.

U.S. Pat. No. 5,480,385 discloses a self-retracting medical needle apparatus, which is comprised a needle unit and a catheter unit received in a hollow handle (container) in the transport position. The catheter unit is covered with a sheath having a tab on its distal end for the transposition of the catheter unit and the needle unit from the transport position into the duty ready position. The needle hub consists of two parts movable and immovable relatively the needle. They are connected with a frangible link. The part, immovable relative to the needle, is movable and hermetically sealed with respect to the interior of the hollow handle. The vacuum arises in the interior of the handle as a result of the needle hub transposition into the duty ready position. This vacuum creates a retracting force, which returns the needle unit into the protection position when the user ruptures the frangible link by a trigger. The movable part of the needle hub in the protection position retains at the hollow handle distal end. The disadvantage of the apparatus is its increased length in the transport position due to the protrusion of the sheath tab distally from the hollow handle distal end as well as increased length of the needle caused by applying the needle hub part movable relative to the needle. Another disadvantage is the unreliability of the retracting mechanism based on the vacuum force, which demands very tight sealing. Such sealing creates unstable friction between the needle hub and the hollow handle leading to jamming of the needle unit on the way to the protection position. The presence of this problem is corroborated with later U.S. Pat. No. 6,086,563 where an attempt was made to solve this problem. Another disadvantage is the increased outside diameter of the hollow handle caused by the necessity to provide free movement of the catheter hub inside the handle because the catheter hub is encircled with the sheath, having an inner thread, as well as a circular engagement recess on the hub movable part, which is located over the sheath. Said increased diameter impedes adjoining the catheter tightly to the patient's skin creating catheterization problems. Another disadvantage is the impossibility of converting the apparatus into the duty ready position by the same hand, which holds the apparatus. Moreover, said conversion is complicated by the necessity to remove the sheath after transposing the catheter unit into the duty ready position. The apparatus has a great number of the details including the sheath, proximal lid of the hollow handle and the means of needle hub sealing. There are very complex details—a needle hub consisting of two parts, a thread, recesses and unusual flash chamber. Along with the above mentioned increased length that adds to material consumption and fabrication complexity increasing the manufacturing cost of the apparatus.

U.S. Pat. No. 6,086,563 discloses Needle retraction mechanism with push start retraction, which includes: a needle unit with a cantilever resilient arm on the needle hub, a catheter unit, a needle cover with distally protruded tip for the transposition of the needle unit from the transport position into the duty ready position (called "extended position" in this patent). The needle unit, the catheter unit and the needle cover are housed in a hollow handle in the transport position. The hollow handle is provided with a trigger member (called "tab" in this patent) interacting with the cantilever arm of the needle hub. There also is a retracting mechanism (called "biasing mechanism" in this patent) founded on creating a vacuum force in the hollow handle as it was made in the previous U.S. Pat. No. 5,480,385. U.S. Pat. Nos. 5,480,385 and 6,086,53 have many of the same deficiencies. One disadvantage is the low reliability of the vacuum retracting mechanism in connection with the friction between the needle hub and the hollow handle. An attempt was made to solve this problem in U.S. Pat. No. 6,086,563 by specially configuring the interacting surfaces of the trigger member and the cantilevered arm. With this method, an axially directed constituent of force is created to overcome the friction force impeding the needle unit movement into the protection position. However, it should be taken into consideration that such a measure is effective only within reach of the trigger member, i. e. over the length of the short distal portion, and cannot overcome a jam in the middle and proximal portions of the hollow handle.

The apparatus according to U.S. Pat. No. 6,086,563 has increased length in the transport position because of the needle cover protruding distally beyond the hollow handle and the trigger member disposition at the distal end of the hollow handle beyond the needle. This apparatus also has a large number of details including the needle cover, a proximal lid of the hollow handle, a rubber cuff of the needle hub, a very complex needle hub with the cantilever arm, a recess for the needle cover engagement, a complicated flash chamber, and the holder of the rubber cuff. The increased length and fabrication complexity add to material consumption and, as a result, the manufacturing cost of the apparatus growths.

Thus, common disadvantages of the apparatuses with the transport position according to the prior art are:

Large length leading to increased material consumption and transportation expenses.

Inconvenience in operation due to the impossibility of controlling the device with one hand.

Low reliability of automatic conversion of the apparatus from the duty ready position into the protection position.

Relatively high manufacturing cost due to a large number of details, their complexity, and great material consumption.

Limitation on the application of catheter various types, in particular the catheters with hub having a side port and wings for attaching the catheter to patient's skin.

Possibility of the needle unit displacement from the protection position leading to personnel infection by blood contaminated needle.

SUMMARY OF THE INVENTION

The objective of the present invention is to reduce the transportation and packaging expenses of the compact catheter insertion apparatus.

Another objective is to allow the apparatus control using one hand.

Another objective is to provide reliable automatic retraction of the needle unit into the protection position.

Another objective is to lower the manufacturing cost of the apparatus by reducing the number of details and their simplifying.

Another objective is eliminating the possibility of the needle accidental dislodging from the protection position.

Another objective is to provide high ergonomics of the apparatus by decreasing the number of manipulations especially the manipulations unaccustomed for the user.

Another objective is extending the application field of various types of the catheter hubs in the catheter insertion apparatus with the transport position including the catheter hubs with a side port and side flexible wings for attaching the catheter hub to patient's skin.

Another objective is eliminating the possibility of the needle unit displacement from the protection position.

The above noted objectives of the present invention are accomplished by the compact catheter insertion apparatus comprising: a needle unit with a needle, a needle distal sharp point, and a needle hub, a catheter unit with a catheter tube and a catheter hub, and a handle. Their mutual dispositions are determined with their transport, duty ready, and protection positions. The apparatus contains a retracting means for the retraction of the needle unit from the duty ready position to the protection position, including a resilient member installed beyond a blood flow between the handle and the needle unit and having a maximal stressed state in the duty ready position.

The apparatus also includes a duty fixation means for releasable fixation of said needle unit to the handle in the duty ready position. This means includes a latch member movable in transverse direction and an immovable engagement member, one of which is disposed on the needle unit and the other on the handle. Moreover, there is a trigger member for actuating said latch member and thereby said retracting means, which in the duty ready position is disposed at the handle distal portion so that there is a possibility to control the trigger member by the same user's hand, which holds the apparatus.

The described retracting means with the resilient member and said trigger member provide reliable automatic retraction of the needle unit into the protection position. At the same time, noted disposition of the trigger member provides one-handed control and enhances the ergonomics level of the apparatus.

The resilient member having the maximal stressed state only in the duty ready position prevents the resilient member's elasticity from the deterioration during the long storage of the apparatus in the transport position. This is due to the minimal stressed state of the resilient member in the transport position. Moreover, this enables the application of inexpensive rubber resilient members in the form of a ring, which are easily secured to the needle unit and the handle. Described rubber resilient member and its disposition are novel and reduce manufacturing cost.

In the developed version embodiment, the latch member, trigger member, and needle hub are made as a single unit. In another version embodiment, the latch member, trigger member, and handle are made as a single unit. As a result, a minimal quantity of apparatus details and a low manufacturing cost are achieved.

The invention includes the version of resilient member disposed eccentrically with respect to the needle, in lower part of the handle under handle internal cavity and beyond the catheter unit in the transport position. This design enables a substantial reduction in the dimensions of the resilient member, particularly in its embodiment as a spiral spring, and reduces the dimensions of the apparatus as a whole. As a result, the manufacturing cost is reduced further. Moreover, said eccentric resilient member location facilitates the use of the catheter hub with a side port and side flexible wings in the apparatus with the transport position. Such application of the noted catheter hubs according to the present invention is novel and extends the application field of the apparatus having the transport position.

The present invention contains a transposing member located on the upper surface of the needle hub. It is designed for manual transposition of the catheter unit from the transport position into the duty ready position. Such disposition of the transposing member shortens the overall length of the apparatus in the transport position reducing transportation and packaging expenses. Moreover, such disposition of the transposing member enhances the convenience of its control as well as reduces the expenses for the manufacturing and the assembly of the apparatus since the transposing member and the needle unit are made as a single unit.

The present invention contains a protection fixation means for the fixation of the needle unit in the protection and transport positions, including the resilient member as well as a springy locking member and a notch located on the needle hub and the handle. Moreover, there is a safety lock means designed for enhancing the reliability of the prevention of the needle distal sharp point from going out of the protection position. In developed version embodiments, the members of said safety lock means are made as a single unit with the trigger member or with the handle and the needle hub and do not increase the number of the details or their cost. The introduction of said safety lock means as an addition to said protection fixation means is novel for devices of this type and completely rules out the possibility of accidental needle exit from the protection position.

In version embodiment, the protection fixation means is made as a non-reversible means eliminating the movement of the needle unit from the protection position without the mentioned additional safety lock means.

BRIEF DESCRIPTION OF THE DRAWINGS

FIGS. 1 to 9 show a compact catheter insertion apparatus, including:
  an eccentric rubber resilient member; trigger and latch members disposed on the handle; a safety means in form of a distal lid of the handle, wherein:
FIG. 1 shows a side elevation of the apparatus in the transport position.
FIG. 2 shows a top plan view of the apparatus in the transport position.
FIG. 3 shows a longitudinal section of the apparatus in the transport position.
FIG. 4 shows a view to the right of the apparatus.
FIG. 5 shows a cross section of the apparatus in the transport position.
FIG. 6 shows a longitudinal section of the apparatus in the duty ready position.
FIG. 7 shows a longitudinal section of the apparatus in the process of the catheter insertion into patient's vein.
FIG. 8 shows the apparatus in the protection position with unclosed a distal handle lid.
FIG. 9 shows the apparatus with operating safety means, that is to say, with closed distal handle lid.

FIGS. 10 to 14 show a compact catheter insertion apparatus, including:
  a resilient means made as a compression spiral spring with a coaxial disposition relative to the handle; latch and trigger members located on the oblong cantilever arm connected with the handle; a safety means made as a notch on the needle hub and a projection on the handle, wherein:
FIG. 10 shows a side elevation of the apparatus in the transport or protection position.
FIG. 11 shows a longitudinal section of the apparatus in the transport position.
FIG. 12 shows a side elevation of the apparatus in the duty ready position.
FIG. 13 shows a longitudinal section of the apparatus in the duty ready position.
FIG. 14 shows a longitudinal section of the apparatus in the protection position.

FIGS. 15 to 20 show a compact catheter insertion apparatus, including:
  a resilient member in form of compression spiral spring of small diameter with eccentric disposition relative to the needle; a latch member disposed on the needle unit; a trigger member disposed on the handle; a safety means made as a locking arm disposed at a distal portion of the handle, wherein:
FIG. 15 shows a side elevation of the apparatus in the transport position.
FIG. 16 shows a top plan view of the apparatus in the transport position.
FIG. 17 shows a longitudinal section of the apparatus in the transport position.
FIG. 18 shows a longitudinal section of the apparatus in the duty ready position.
FIG. 19 shows a longitudinal section of the apparatus in the process of the catheter insertion into patient's vein.
FIG. 20 shows a longitudinal section of the apparatus in the protection position with operating safety means, that is to say, with the locking arm turned downward.

FIGS. 21 to 28 show a compact catheter insertion apparatus, including:
  resilient member made as a rubber member with eccentric disposition relative to the needle axis; intermediate bush having an engagement member of the duty fixation means and serving as well as a safety means; a latch and trigger members disposed on the needle hub; a catheter hub with central and side ports and with side foldable wings, wherein:
FIG. 21 shows a top plan view of the apparatus in the transport position.
FIG. 22 shows a side elevation of the apparatus in the transport position.
FIG. 23 shows a longitudinal section of the apparatus in the transport position.
FIGS. 24, 25 show cross sections of the apparatus in the transport position.

FIG. 26 shows a longitudinal section of the apparatus in the duty ready position.

FIG. 27 shows a longitudinal section of the apparatus in the process of the catheter insertion into patient's vein.

FIG. 28 shows a longitudinal section of the apparatus in the protection position.

FIGS. 29 to 39 show a compact catheter insertion apparatus including a catheter with central and side ports and side foldable wings, as well as with non-reversible protection fixation means, wherein:

FIG. 29 shows a side elevation of the apparatus in the transport position.

FIG. 30 sows a top plan view of the apparatus in the transport position.

FIG. 31 shows a longitudinal section of the apparatus in the transport position.

FIGS. 32, 33, 34, 35 show cross sections of the apparatus in the transport position.

FIG. 36 shows a top plan view of the apparatus in the duty ready position.

FIG. 37 shows a longitudinal section of the apparatus in the duty ready position.

FIG. 38 shows a longitudinal section of the apparatus in the process of the catheter insertion into patient's vein.

FIG. 39 shows a longitudinal section of the apparatus in the protection position.

FIGS. 40 to 46 show a compact catheter insertion apparatus including a catheter with side foldable wings and non-reversible protection fixation means of version embodiment, wherein:

FIG. 40 shows a side elevation of the apparatus in the transport position.

FIG. 41 shows a longitudinal section of the apparatus in the transport position.

FIGS. 42, 43 show cross sections of the apparatus in the transport position.

FIG. 44 shows a side elevation of the apparatus in the duty ready position with the section of the handle.

FIG. 45 shows a top plan view of the apparatus in the duty ready position.

FIG. 46 shows a longitudinal section of the apparatus in the protection position.

DETAILED DESCRIPTION OF THE INVENTION

Figure 1:
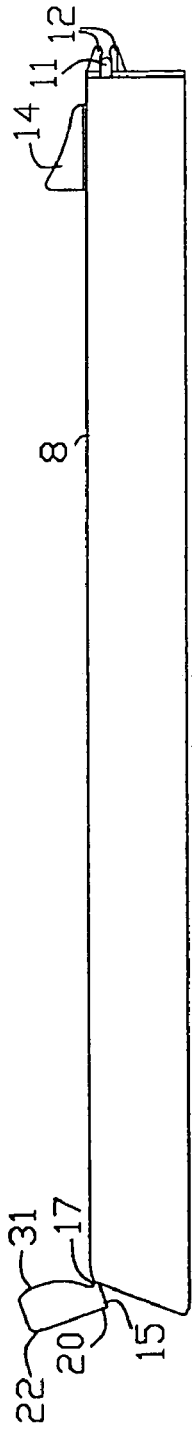
Figure 2:
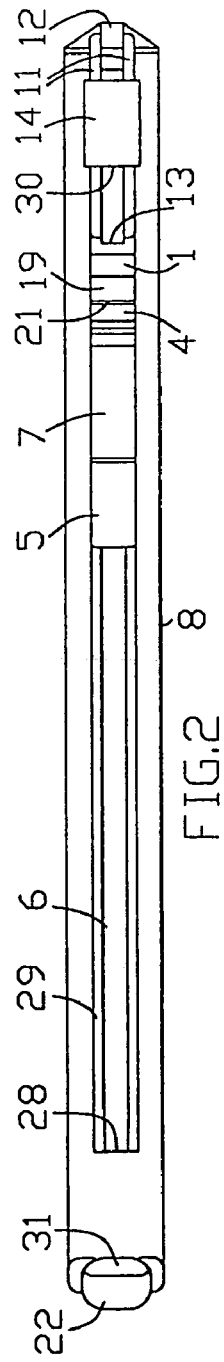

A circumstantial explanation of the present invention is offered with reference made to the attached drawings.

The compact catheter insertion apparatus shown in FIGS. 1 to 9 is comprised of: a needle unit 1 with a needle 2, a needle distal sharp point 3 and a needle hub 4, affixed to a proximal end of the needle 2; a catheter unit 5 with a catheter tube 6 and a catheter hub 7 affixed to a proximal end of the catheter tube 6; a handle 8.

Figure 3:
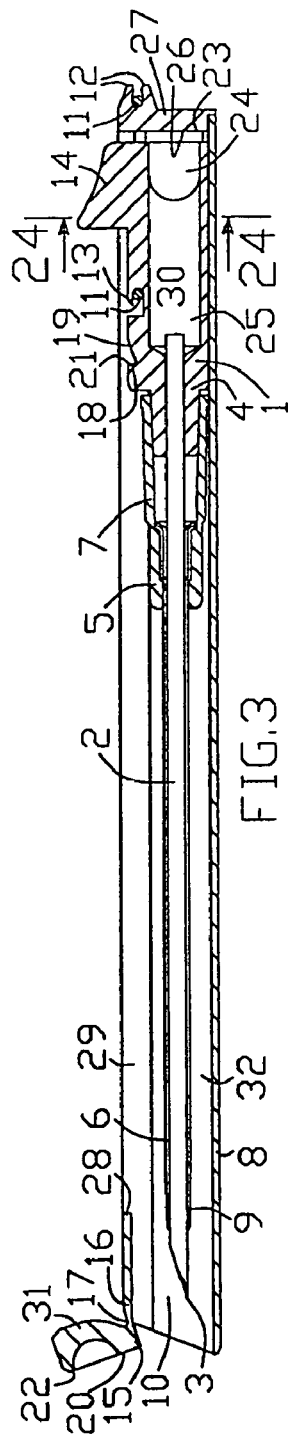
Figure 4:
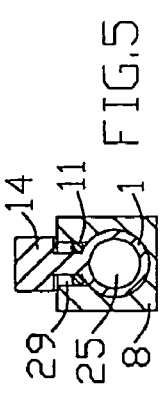
Figure 5:
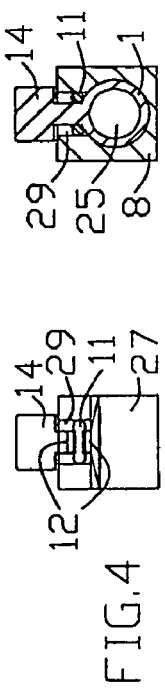
Figure 10:
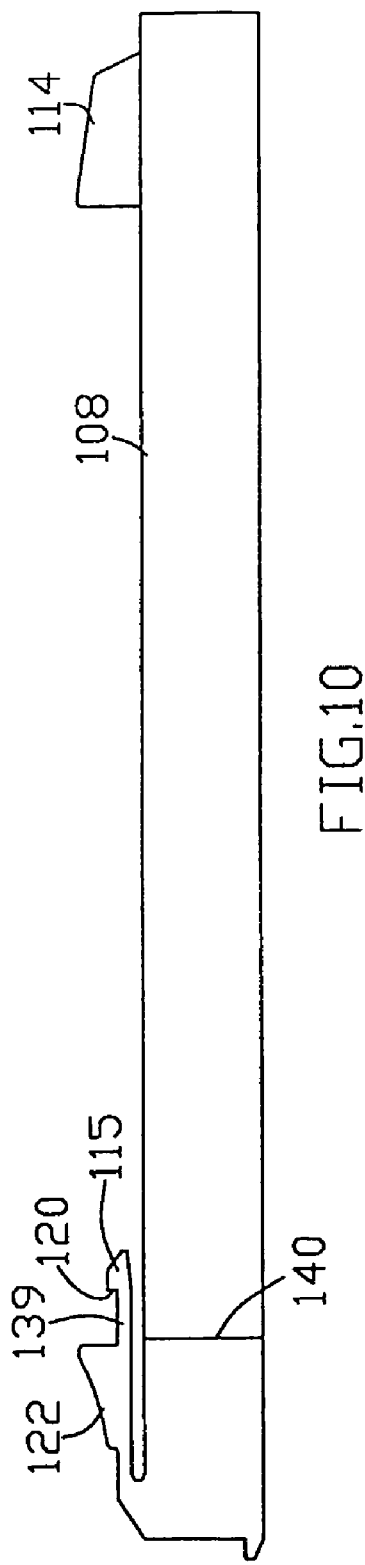

Mutual disposition of needle unit 1, catheter unit 5 and handle 8 is determined with their transport position shown in FIGS. 1 to 5, duty ready position shown in FIG. 6, and protection position shown in FIG. 9. In the transport position needle 2 is housed inside catheter tube 6, catheter unit 5 is disposed in the extreme proximal position with respect to handle 8 and needle distal sharp point 3 is protected against any contact (FIG. 3). In the duty ready position, needle 2 is housed inside catheter tube 6 so that needle distal sharp point 3 protrudes distally outside of distal end 9 of catheter tube 6 and needle hub 4 is disposed in a distal extreme position with respect to handle 8 and removably fixed to it (FIG. 6). In the protection position, needle unit 1 is separated from catheter unit 5 and retracted from the duty ready position in a proximal direction with respect to handle 8 so that needle distal sharp point 3 is positioned in security zone 10, which is located at the distal part of handle 8 and protects needle distal sharp point 3 from any contacts with persons (FIGS. 8, 9).

The apparatus also comprises: a protection fixation means for the fixation of needle unit 1 with respect to handle 8 in the transport and protection positions; a duty fixation means for the releasable fixation of needle unit 1 to handle 8 in the duty ready position; a transposing means for the transposition of catheter unit 5 and needle unit 1 from the transport position into the duty ready position; a limiting means for the prevention of needle unit 1 from excessive going out of handle 8 in a distal direction for the transposition of needle unit 1 to the duty ready position; a retracting means for the retraction of needle unit 1 from the duty ready position into the protection position; a trigger member for actuating the retracting means; a safety means for enhancing the reliability of the prevention of needle distal sharp point 3 in the protection position from going out of security zone 10 and from any contact with persons.

Noted retracting means includes resilient member 11 installed beyond a blood flow between hook members 12 of handle 8 and hook member 13 of needle unit 1. Resilient member 11 interacts with handle 8 and needle unit 1 and has a minimal stressed state in the transport position (FIGS. 2, 3) and the protection position (FIGS. 8, 9) and a maximal stressed state in the duty ready position (FIG. 6). This way, the deterioration of the resilient member elasticity for long storage of the apparatus in the transport position is avoided. It also allows an inexpensive, rubber resilient member to be used. Resilient member 11 is a rubber member, circular and solid in its cross section and made in form of a ring. Resilient member 11 is easily secured to needle unit 1 and handle 8 by means of hook members 12 and 13. Resilient member 11 relates to the extension pulling members. Another feature of resilient member 11 is its eccentric disposition beyond the catheter unit in the transport position (FIGS. 2, 3) that reduces the apparatus overall dimensions.

In version embodiments, the rubber resilient member is made: as a single linear member with a loop at each of its ends adapted to securing with the hook members similar to members 12, 13 and located on needle unit 1 and handle 8 (not shown); as a single linear member of solid or tubular cross section provided with an anchor member at each of its end and made as a local thickening adapted to securing with coupling means located on needle unit 1 and handle 8 (not shown).

The above noted transposing means includes transposing member 14, which presents a member located on the lateral surface of needle hub 4 and adapted to the effect by user's finger to transpose needle unit 1 from the transport position to the duty ready position.

The above noted duty fixation means includes latch member 15 located on handle 8 and connected with its distal end 16 by elastic member 17 allowing to turn latch member 15 around elastic member 17. Owing to the elasticity of elastic member 17, latch member 15 is movable in a direction transverse relative to the axis of needle 2. The duty fixation means also includes engagement member 18 located in recess 19 on the lateral surface of needle hub 4 and immovable relative to needle hub 4. As a result of the transposition of needle unit 1 from the transport position into the duty ready position, latch member 15 and engagement member 18 engage (FIG. 6) and thereby provide the fixation of needle unit 1 relative to handle 8 in the duty ready position. In this state, latch member 15 and engagement member 18 interact with each other by operating surface 20 of the latch member facing distally and operating surface 21 of the engagement member facing proximally. Due to its elastic properties, elastic member 17 also provides the keeping force, which, in the duty ready position, is directed towards the axis of needle hub 4. Said keeping force provides the introduction of latch member 15 into the engagement with engagement member 18 and keeps them in the engaged state in the duty ready position.

Above noted trigger member 22 presents the extension of latch member 15 upwards (FIGS. 1 to 8). Trigger member 22 in the duty ready position (FIG. 6) is disposed at the distal end of handle 8 so that there is a possibility to control trigger member 22 by the same user's hand, which holds the apparatus at its handle 8. Holding the apparatus in the duty ready position, the user introduces needle distal sharp point 3 into patient's vein and displaces catheter unit 5 relative to needle 2 in the distal direction as it is shown in FIG. 7. Then, user presses trigger member 22 in the proximal direction by a finger of the hand, which holds the apparatus. As a result, latch member 15 and engagement member 18 are disengaged and needle unit 1 under an effect of resilient member 11 is retracted automatically into the protection position shown in FIG. 8. Thus, user implements the apparatus control using only one hand and the retraction of needle unit 1 into the protection position is accomplished automatically.

The above noted protection fixation means includes resilient member 11, which in the protection and transport positions prevents needle unit 1 from the displacement in a distal direction relative to handle 8. It also includes a proximal protection fixation means preventing needle unit 1 in the transport and protection positions from the displacement in a proximal direction relative to the handle. This means comprises distal stopping member 23 presenting the proximal face of plug 24 of flash chamber 25 located in needle hub 4 and a proximal stopping member presenting the distal face 26 of proximal lid 27 of handle 8.

The above noted limiting means contains distal limiting member 28 presenting the distal face of longitudinal slot 29 in handle 8 and proximal limiting member 30 presenting the proximal face of transposing member 14. The limiting members abut against each other at the end of the transposition stroke preventing needle unit 1 from going out in a distal direction.

The above noted safety means presents distal lid 31 of handle 8, which in the protection position is manually closed as it is shown in FIG. 9. Lid 31 relates to the safety limiting means restricting the mobility of the needle distal sharp point and the access to it with the restrictive barriers. Lid 31 as a distal barrier prevents the needle distal sharp point from going outside security zone 10 in a distal direction.

The apparatus shown in FIGS. 1 to 9 has distal handle lid 31, elastic link 17, latch member 15, trigger member 22, limiting member 28, and handle 8 made of plastics as a single unit. Moreover, needle hub 4, transposing member 14, engagement member 18, hook member 13, and limiting member 30 are made as a single unit. As a result, the construction of the apparatus consists of few relatively simple details leading to the apparatus low manufacturing cost.

Handle 8 of the apparatus presents an oblong body with internal cavity 32 of a circular cross section, which houses needle unit 1 and catheter unit 5 in the transport position, serves as a guide for needle hub 4, and has longitudinal slot 29 for movable location and the transposition of transposing member 14.

FIGS. 10 to 14 show the version embodiment of the compact catheter insertion apparatus, which has the same means and many identical details in comparison with the previous version. Therefore, these details have similar designations distinguished only by the addition of the numeral 100. The distinctions of said version embodiment are considered below.

Resilient member 111 relates to the compression pushing members and is made as a compression spiral spring axially disposed relative to needle 102. Catheter hub 107 is disposed inside spring 111 in the transport position and spring 111 allows a free transposition of the catheter hub from the transport position to the duty ready position (FIGS. 11, 13).

The duty fixation means includes oblong elastic cantilever arm 139 extending along the distal portion of handle 108 outside of it, connected with handle 108 by its distal end and having latch 115 on its proximal end and trigger member 122 on its middle portion. Trigger member 122 is made as the lug of arm 139 protruding in the direction opposite handle 108. The duty fixation means also includes engagement member 118, which is made as a single unit with transposing member 114 and located over arm 139 in the duty ready position (FIG. 13). Cantilever arm 139 fulfils the keeping means role by creating the keeping force directed to the side opposite relative to handle 108 and, at the same time, cantilever arm 139 provides the mobility of latch 115 in the transverse direction owing to its elasticity. Latch member 115 and engagement member 118 have interacting surfaces 120 and 121 respectively.

Figure 11:
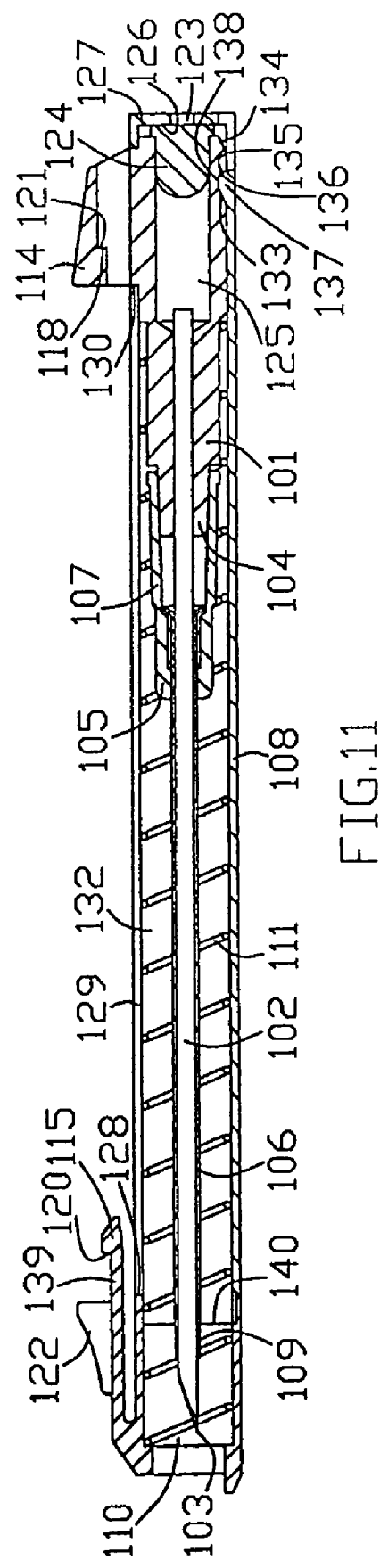
Figure 15:
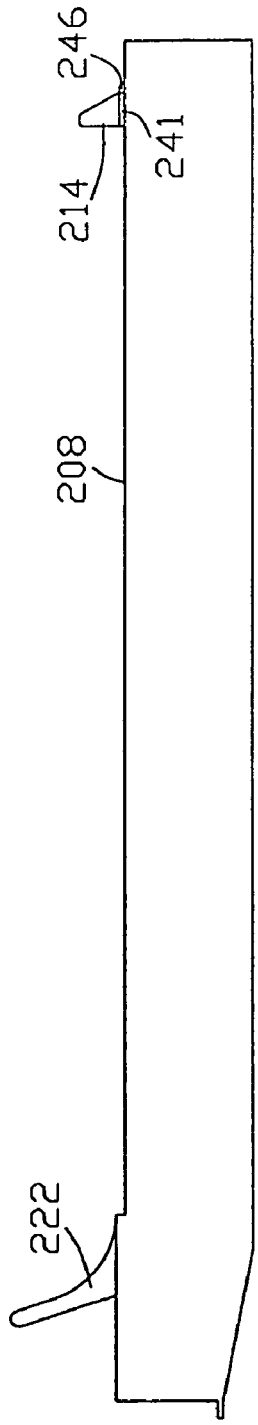
Figure 16:
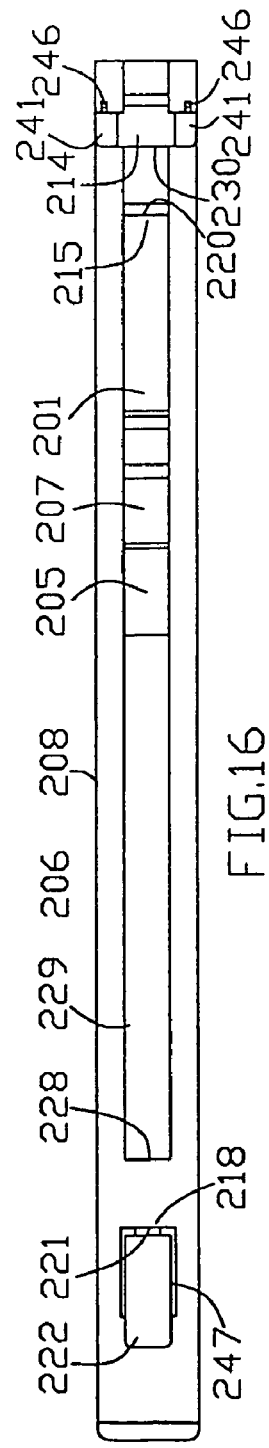
Figure 17:
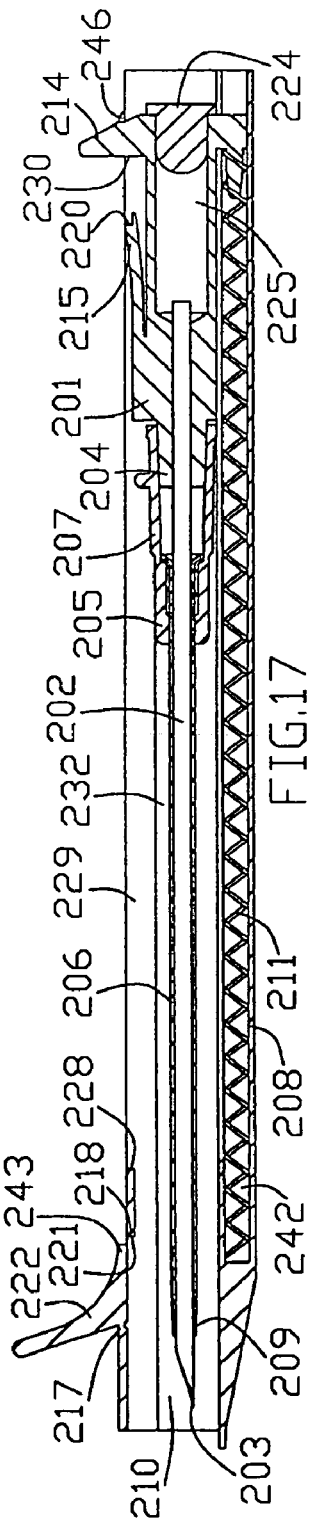
Figure 29:
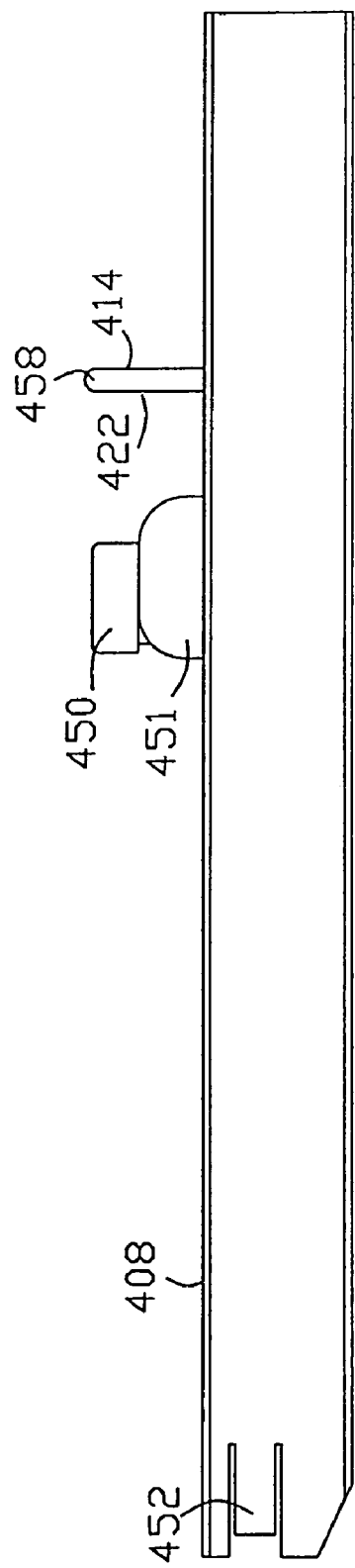
Figure 30:
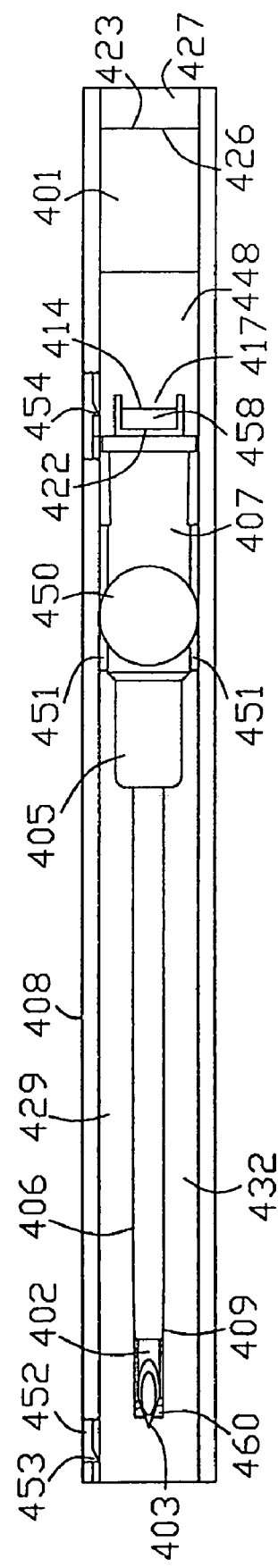
Figure 36:
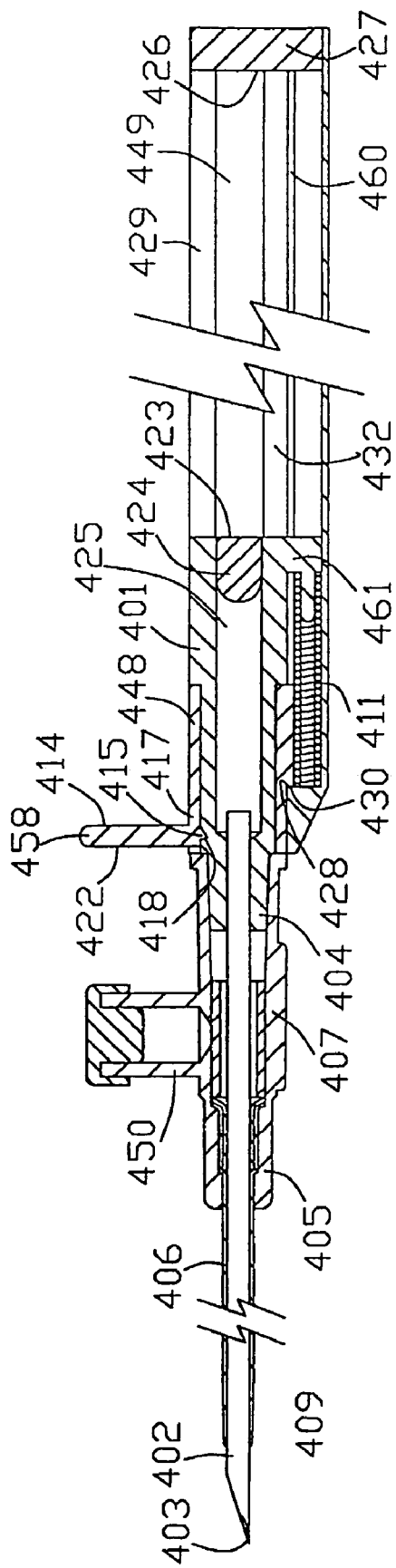
Figure 37:
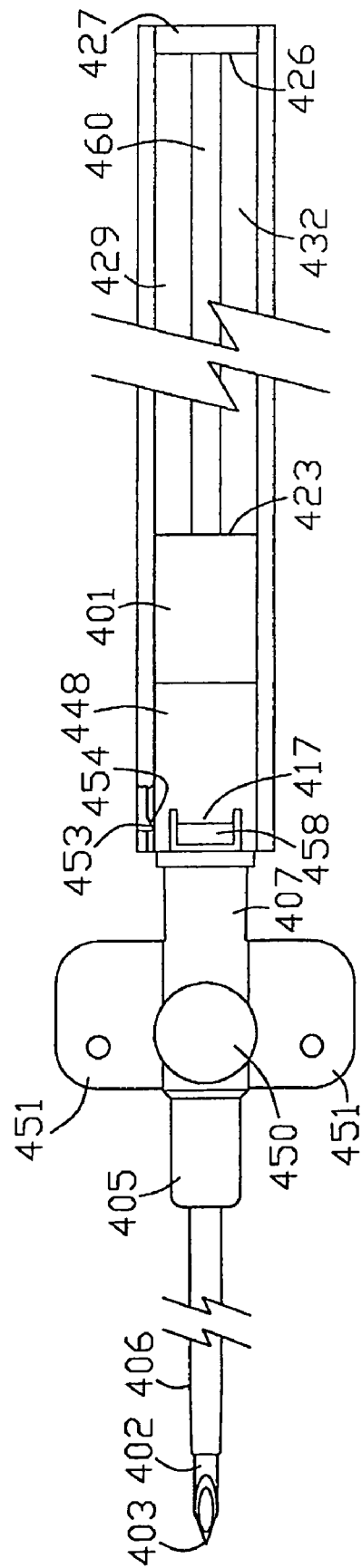

The safety means of the apparatus, according to FIGS. 10 to 14, presents the safety locking means increasing the engagement between needle 102 and handle 108 and their mutual immobility in the protection position. This means includes the automatic locking members made as projection 137 on handle 108 and notch 138 on needle unit 101, which become engaged in the transport and protection positions (FIGS. 11, 14). These locking members have surfaces 133 and 134, which interact during the introduction of projection 137 and notch 138 into engagement. Surfaces 133 and 134 are disposed at a relatively small angle, approximately 30°, to the axis of handle 108. This provides a low resistance, surmountable by spring 111 during said introduction of locking members 137 and 138 into the engagement. Surfaces 135, 136 of locking members 137, 138 also interact during the disengagement of locking members 137, 138 during the transposition of the needle unit into the duty ready position. These surfaces are disposed at a relatively high angle, approximately 60°, to the axis of handle 108. Therefore, they provide a relatively high, but manually surmountable, resistance during the disengagement of locking members 137, 138. Said high resistance prevents needle distal sharp point 103 from accidentally existing security zone 110 in the transport and protection positions.

Note, that latch member 115, trigger member 122, cantilever arm 139, distal limiting member 128, locking member 137, and handle 108 present a single unit. According to the fabrication technology, handle 108 is made as two part joined by seam 140. Moreover, transposing member 114, engagement member 118, proximal limiting member 130, locking member 138, and needle unit 101 are made as a single unit. The minimization of details number results in low manufacturing cost.

The other means of the apparatus according to FIGS. 10 to 14 are identical to the previous version.

The version embodiment of the apparatus shown in FIGS. 15 to 20 has the designations of the details with the first numeral 2. The description of the previous version relates to the part of present version details with identical second and third numerals. At the same time, the present version has some distinctions, which are considered below.

Resilient member 211 presents a compression pushing member made as a compression spiral spring, disposed lengthwise of handle 208 eccentrically with respect to needle 202 and beyond catheter unit 205 in the transport position. The eccentric disposition results in a substantial decrease in the diameter of spring 211, which, in the present version, constitutes approximately 18% of the handle 108 diameter. This creates new possibilities for the general arrangement of the apparatus details leading to the reduction of the apparatus size and manufacturing cost. It also facilitates the application of the catheter hub with a side port and side flexible wings.

The duty fixation means includes latch member 215, which is disposed on needle hub 204 made in the form of elastic arm and has operating surface 220 facing proximally. This means also includes engagement member 218 with operating surface 221 facing distally. Operating surface 221 is located in longitudinal notch 247 at the distal portion of handle 208. Said elastic arm also fulfils the keeping means role creating the keeping force directed from handle 208.

The safety means presents the safety lock means comprising manually controlled locking arm 243 made as a single unit with trigger member 222, disposed at the distal portion of handle 208 and connected with it by elastic link 217. After the insertion of catheter unit 205 into the patient's vein (FIG. 19), user turns locking arm 243 downward by trigger member 222 and thereby disengages latch member 215 and engagement member 218. As a result, needle unit 201, under the effect of spring 211, is automatically retracted into the protection position (FIG. 20). After that, user turns locking member 243 clockwise thereby pressing the needle 202 to the internal wall of handle 208 and ruling out any displacement of needle 202 relative to handle 208.

Transposing member 214 is provided with elastic lateral plates 241 (FIGS. 15, 16) interacting with stopping members 246. Stopping members 246 have proximal inclined surfaces 245 (FIG. 19) adapted to surmounting the stopping members 246 by lateral plates 241 during the introduction of needle unit 201 into handle 208 for their assembly. Stopping members 246 also have distal sheer surfaces 244, which make stopping members 246 insurmountable by lateral plates 241 during the retraction of needle unit 201 into the protection position. The presence of stopping members 246 enables the exclusion of the proximal handle lid from the apparatus thereby reducing its total detail number and manufacturing cost.

The version embodiment of the apparatus according to FIGS. 21 to 28 has the designations of the details with the first numeral 3. The description of the previous versions relates to the part of the present version details with identical second and third numerals. At the same time, the present version has some distinctions, which are considered below.

The retracting means includes rubber resilient member 311 akin to resilient member 11 in FIGS. 1 to 9.

Catheter hub 307 includes side port 350 and two flexible side wings 351 for fixing the catheter hub to the patient's skin. Internal cavity 332 of handle 308 has the form in its cross section (FIGS. 24, 25) adapted to receiving catheter hub 307 with side port 350 and flexible side wings 351. Specifically, handle 308 contains internal lateral guide grooves 349 for movable receiving guide ridges 355 of needle hub 304 and 356 of intermediate bush 348 (see as well FIG. 21). Moreover, handle 308 has sufficiently broad elongated slot 329 for movable location and transposition of side port 350 and flexible side wings 351 inside it.

The duty fixation means includes engagement member 318 with operating surface 321 disposed on intermediate bush 348, which is immovably connected with handle 308 in the duty ready position (FIG. 26). The duty fixation means also includes lath member 315 with operating surface 320 disposed on one of two arms of lever 357. The second arm of lever 357 presents trigger member 322. Lever 357 is connected with needle hub 304 by elastic link 317. In the transport position (FIGS. 21 to 23), lath member 315 and engagement member 318 are engaged under the effect of the keeping force creating by elastic link 317 and stopping members 323 and 326 abut against each other under the effect of resilient member 311. User transposes needle unit 301 into the duty ready position by means of transposing member 314. Therewith, limiting members 328, 330 prevent needle unit 301 from excessive going out of handle 308 in a distal direction. In the duty ready position (FIG. 26), notches 354 of intermediate bush 348, shown in FIG. 21, come into the engagement with ridges 353 located on elastic plates 352 of handle 308. As a result, the fixation of the intermediate bush relative to handle 308 is accomplished. User then displaces catheter unit 305 into the patient's vein (FIG. 27) and then disengages latch member 315 and engagement member 318 by means of trigger member 322. As a result, resilient member 311 retracts needle unit 301 into the protection position (FIG. 28) and needle distal sharp point 303 enters security zone 310 located in intermediate bush 348, which remains at the distal end of handle 308. In this position, intermediate bush 348 presents the safety means restricting access to needle distal sharp point 303 and its radial movement due to the small diameter of intermediate bush 348.

The version embodiment of the apparatus according to FIGS. 29 to 39 has the designations of the details with the first numeral 4. The description of the previous versions mainly relates to the part of the present version details with identical second and third numerals. At the same time, the present version has specific distinctions, which are considered below.

The retracting means includes compression spring 411 located eccentrically with respect to the axis of needle 402 underneath of handle internal cavity 432 and connected with needle unit by connecting member 461 movably passing through lower slot 460.

Catheter hub 407 includes the side port 450 and two foldable side wings 451 for fixing the catheter hub to the patient's skin. Internal cavity 432 of handle 408 has the form in its cross section adapted to receiving catheter hub 407 with side port 450 and folded side wings 451 (FIG. 34). Specifically, handle 408 contains internal lateral guide grooves 449 for movable receiving the guide ridges 455 of intermediate member 448 and the guide ridges (not shown) of needle unit 401 located proximally of ridges 455. Moreover, handle 408 has elongated slot 429 sufficiently broad for movable location and transposition of side port 450 and folded side wings 451 inside it.

The duty fixation means includes engagement member 418 in the form of a notch on needle unit 401 and lath member 415 disposed on lever 458, which is connected with intermediate member 448 by elastic portion 417 (FIGS. 31, 36, 37, 38). The upper portion of lever 458 fulfils a role of trigger member 422 designed for pressing on its distal side and simultaneously a role of transposing member 414 designed for pressing on its proximal side. In the transport position (FIGS. 29-35), lath member 415 and engagement member 418 are engaged under the effect of the keeping force creating by elastic portion 417, and stopping members 423 and 426 abut against each other under the effect of spring 411. User transposes needle unit 401 into the duty ready position by means of transposing member 414. Therewith, limiting members 428, 430 prevent needle unit 401 from excessive going out of handle 408 in a distal direction. In the duty ready position (FIGS. 36, 37), notches 454 of intermediate member 448 come into the engagement with ridges 453 located on elastic plates 452 of handle 408. As a result, the fixation of intermediate member 448 relative to handle 408 is accomplished. User then inserts catheter unit 405 into patient's vein (FIG. 38) and, after this, disengages latch member 415 and engagement member 418 by means of trigger member 422. As a result, spring 411 retracts needle unit 401 into protection position (FIG. 39) and needle distal sharp point 403 enters security zone 410 located in intermediate member 448, which remains at the distal end of handle 408. Needle unit 401 is held in the protection position by spring 411 without any means allowing needle unit transposition in a distal direction from the protection position as its transposing member 414 has remained in the previous duty ready position. Thus, the embodiment of lever 458 and latch member 415 provides the disconnection of needle unit 401 and transposing member 414 during actuating trigger member 422 thereby converting the protection fixation means into non-reversible means, which eliminate the displacement of needle unit 401 relative to handle 408 in a distal direction from the protection position.

The version embodiment of the apparatus, according to FIGS. 40 to 46, has the designations of the details with the first numeral 5. The description of the previous versions mainly relates to the part of the present version details with identical second and third numerals. At the same time, the present version has specific distinctions, which are considered below.

The retracting means includes rubber resilient member 511 in the form of a ring located mainly inside handle 508 closely to its lower wall. In the transport position, resilient member 511 is disposed at the proximal end of handle 508 and its distal end is attached to needle hub 501 adjacently to the proximal end of catheter hub 507 (FIG. 41).

The duty fixation means includes oblong elastic cantilever arm 539 extending along handle 508 over it, connected with needle unit 501 through longitudinal slot 529 in handle internal cavity 532, and having latch 515 and trigger member 522 on its distal portion as well as transposing member 514 on its proximal end. The duty fixation means also includes engagement member 518, which is made as a single unit with handle 508 and located at the distal portion of handle 508 over it.

Catheter hub 507 includes two foldable side wings 551 for fixing the catheter hub to the patient's skin. Handle internal cavity 532 is adapted to movable receiving catheter hub 507 with side wings 551, which, in the transport position, are folded in a distal direction underneath catheter hub 507.

User transposes needle unit 501 and catheter unit 505 into the duty ready position pressing onto transposing member 514. In the duty ready position, latch 515 and engagement member 518 engage fixing the duty ready position, and side wings 551 go out of handle internal cavity 532 and straighten (FIGS. 44, 45). After inserting catheter tube 506 into patient's vein, user presses down onto trigger member 522 thereby disengaging latch 515 and engagement member 518 and allowing resilient member 511 to retract needle unit 501 into protection position (FIG. 46).

The protection fixation means of the apparatus presents a non-reversible means eliminating the displacement of needle unit relative to handle 508 in a distal direction from the protection position. This means includes the locking member in the form of projection 537 located on elastic portion 559 of the handle cavity internal wall and notch 538 on needle unit 501. Projection 537 has inclined distal surface 533, which is faced proximally and interacts with the proximal end of needle unit 501 in the transport position and during the retraction of needle unit 501 into the protection position. In the transport position, needle unit 501 is located distally of surface 533 because the force of resilient member 511 is insufficient to deflect elastic portion 559 and surmount surface 533 (FIG. 41). During needle unit retraction into the protection position, the sum of resilient member force and needle unit inertia force is sufficient to surmount surface 533 by needle unit proximal end. As a result, projection 537 and notch 538 engage in the protection position (FIG. 46). Projection 537 and notch 538 have proximal surfaces 535 and 536 inclined with respect to the needle axis at such angle, e. g. 90°, which eliminates their disengagement upon pushing needle unit 501 in a distal direction.

The invention claimed is:

1. A compact catheter insertion apparatus, said apparatus comprising:
 a needle unit having a needle with a needle distal sharp point and a needle proximal end, a needle hub attached to said needle proximal end, and a flash chamber located inside said needle hub and having a porous membrane permeable to air and non-permeable to blood;
 a catheter unit having a catheter tube and a catheter hub affixed to a catheter tube proximal end;
 a handle serving as a guide and a receptacle for said needle and catheter units;
 a security zone located at said handle distal end, wherein said needle distal sharp point is protected from contact with persons when the needle distal sharp point is in said security zone;
 said needle unit, catheter unit, and handle are operable to be disposed in a transport position, a duty ready position, and a protection position, wherein:
  in said transport position said needle and said catheter unit are disposed within the axial limits of said handle, said needle is disposed inside said catheter tube so that said needle distal sharp point protrudes distally of the distal end of said catheter tube, said catheter unit is disposed in an extreme proximal position with respect to said handle, said needle hub is disposed near said handle proximal end, and said needle distal sharp point is disposed in said security zone;
  in said duty ready position said needle unit is releasably affixed to said handle adjacent to said handle distal end, said catheter hub at least partly protrudes out of said handle in a distal direction thereby providing the user's immediate access and the immediate control of said catheter hub by user's hand;
 in said protection position said needle distal sharp point is positioned in said security zone;
 a transposing member attached to said needle unit, extending outside of said handle, to be effected by user's finger for manual transposition of said catheter unit and needle unit from said transport position into said duty ready position;
 a duty fixation means for releasable affixing said needle unit adjacent to said handle distal end in said duty ready position;
 a resilient retracting means for the retraction of said needle unit from said duty ready position into said protection position including a resilient member installed beyond a blood flow and having maximum stressed state in said duty ready position;
 a trigger member for actuating said retracting means, wherein in said duty ready position said trigger member is disposed at the distal part of said handle, wherein a single hand of an associated user may control said trigger member and also holds the apparatus.

2. The apparatus of claim 1, wherein said handle has a longitudinal internal cavity, in which said catheter unit is located in said transport position, said needle unit is located in said transport and protection positions, said needle hub at least partly is located in said duty ready position, and there is a longitudinal slot in said internal cavity wall, through which said transposing member extends.

3. The apparatus of claim 2, wherein the resilient member is made of elastic polymer like rubber and secured to said needle hub and handle by a coupling means.

4. The apparatus of claim 3, wherein said resilient member has a ring form and said coupling means are made as protrusions, one of which is located on said needle hub and the other is located at said handle proximal end.

5. The apparatus of claim 2, wherein said resilient member is an extension spiral spring.

6. The apparatus of claim 2, wherein said resilient member is a compression spiral spring disposed lengthwise in said handle.

7. The apparatus of claim 6, wherein said catheter hub in said transport position is disposed beyond said spring.

8. The apparatus of claim 6, wherein said catheter hub in said transport position is disposed inside said spring, and said spring allows free transposition of said catheter hub from said transport position to said duty ready position.

9. The apparatus of claim 2, wherein said catheter hub is provided with two flexible side wings for securing said catheter hub to patient's skin, said side wings are foldable and said handle longitudinal internal cavity has form and dimensions adapted to movable receiving said catheter hub with folded said side wings.

10. The apparatus of claim 2, wherein said handle longitudinal slot is open from the distal face of said handle.

11. The apparatus of claim 10, wherein said catheter hub has a side port protruding outside said handle through said handle longitudinal slot in said transport position.

12. The apparatus of claim 11, wherein an intermediate bush is located proximally of said catheter tube in said transport and duty ready positions and the intermediate bush is movably operable with said catheter and needle unit during transposition from said transport position into said duty ready position, and said intermediate bush remains at said handle distal end in said protection position for forming a portion of said security zone and restricting accidental personnel contact with said needle distal sharp point.

13. The apparatus of claim 2, wherein said duty fixation means includes a latch member and an engagement member, wherein the latch member and the engagement member cooperatively interact such that when one of the latch member and the engagement member is disposed on said needle unit in said duty ready position, the other is disposed on an element that is immovable relative to said handle at least in said duty ready and protection positions.

14. The apparatus of claim 2, further including a protection fixation means for the fixation of said needle unit in said protection position.

15. The apparatus of claim 14, wherein said resilient member presents said protection fixation means preventing said needle unit from spontaneous displacement in a distal direction relative to said handle.

16. The apparatus of claim 15, wherein said protection fixation means is formed by a springy locking member and a notch, wherein one of the springy locking member and the notch is disposed on said needle unit and the other is located on said handle so that the engagement of the springy locking member and the notch in said protection position prevents said needle unit from the displacement in a distal direction relative to said handle.

17. The apparatus of claim 2 further including a transport fixation means for the fixation of said needle unit relative to said handle in said transport position.

18. The apparatus of claim 17, wherein said resilient member in said transport position presents said transport fixation means preventing said needle unit from spontaneous displacement in said distal direction relative to said handle.

19. The apparatus of claim 2 further including a safety lock means additionally locking said needle unit in said protection position and thereby eliminating a spontaneous displacement of said needle unit distally from said protection position.

20. The apparatus of claim 16, wherein said safety lock means presents a lid secured to said handle distal end by an elastic link and in said protection position said lid is manually closed creating a distal barrier hampering the displacement of said distal sharp point outside of said security zone in a distal direction.

21. The apparatus of claim 2, wherein said transposing member is detached from said needle hub after transposing said needle unit into said duty ready position, but not before activation of said trigger member, where said detachment results in elimination of repeated transposition of said needle unit (1) from said protection position into the duty ready position.

22. The apparatus of claim 13, wherein said latch member and trigger member are made as a single detail so that the activation of said trigger member disengages said latch member and said engagement member.

23. The apparatus of claim 2, wherein said trigger member is disposed on said needle unit and said needle hub and trigger member are made as a single detail.

24. The apparatus of claim 2, wherein said trigger member is disposed on an immovable element relative to said handle while apparatus is in at least said duty ready and protection positions.

25. The apparatus of claim 24, wherein said trigger member and said handle are made as a single detail.

26. The apparatus of claim 2, wherein a proximal force applied to the trigger member in the duty ready position activates the trigger member.

27. A compact catheter insertion apparatus, comprising:
a needle unit having a needle with a needle distal sharp point and a needle proximal end to which a needle hub is attached; a handle having a longitudinal internal cavity;
a catheter unit having a catheter tube and a catheter hub affixed to a catheter tube proximal end, said catheter hub is provided with two foldable side wings for securing said catheter hub to patient's skin, and said catheter hub with said folded side wings has a transverse dimension less than the longitudinal internal cavity of the handle;
a security zone located at said handle distal end, wherein said needle distal sharp point is protected from contact with persons when the needle distal sharp point is in said security zone;
said needle unit, catheter unit, and handle are operable to be disposed in a transport position, a duty ready position, and a protection position, wherein:
in said transport position said needle and said catheter unit are disposed within the axial limits of said handle, said needle is disposed inside said catheter tube so that said needle distal sharp point protrudes distally of the distal end of said catheter tube, said catheter unit is disposed in an extreme proximal position with respect to said handle, said needle hub is disposed near said handle proximal end, and said needle distal sharp point is disposed in said security zone;

in said duty ready position said needle unit is releasably affixed to said handle adjacent to said handle distal end, said catheter hub at least partly protrudes out of said handle in a distal direction thereby providing the user's immediate access and the immediate control of said catheter hub by user's hand;

in said protection position said needle distal sharp point is positioned in said security zone;

a transposing member attached to said needle unit, extending outside of said handle, to be effected by user's finger for manual transposition of said catheter unit and needle unit from said transport position into said duty ready position;

a duty fixation means for releasable affixing said needle unit adjacent to said handle distal end in said duty ready position;

a resilient retracting means for the retraction of said needle unit from said duty ready position into said protection position including a resilient member installed beyond a blood flow and having maximum stressed state in said duty ready position;

a trigger member for actuating said retracting means, wherein in said duty ready position said trigger member is disposed at the distal part of said handle, wherein a single hand of an associated user may control said trigger member and also holds the apparatus.

28. The apparatus of claim 27, wherein said resilient member is disposed eccentrically relative to the axis of said needle.

29. The apparatus of claim 28, wherein said handle longitudinal internal cavity has a longitudinal slot and there is a transposing member designed for manual transposition of said catheter unit and needle unit from said transport position into said duty ready position, located on the lateral surface of said needle unit, extending through said handle longitudinal slot to the outside, and adapted to the effect by user's finger.

30. The apparatus of claim 29, wherein said handle internal cavity and said longitudinal slot have the form and dimensions adapted to movable location and transposition of said catheter hub with said folded side wings.

31. The apparatus of claim 30, wherein said catheter hub along with a central port includes a side port, wherein said handle internal cavity and longitudinal slot are adapted to be movably located and transposed in said side port.

* * * * *